US011038098B2

(12) United States Patent
Tseng et al.

(10) Patent No.: US 11,038,098 B2
(45) Date of Patent: *Jun. 15, 2021

(54) MAGNETIC RANDOM ACCESS MEMORY WITH VARIOUS SIZE MAGNETIC TUNNELING JUNCTION FILM STACKS

(71) Applicant: TAIWAN SEMICONDUCTOR MANUFACTURING CO., LTD., Hsinchu (TW)

(72) Inventors: Huang-Wen Tseng, Zhubei (TW); Cheng-Chou Wu, Hsinchu (TW); Che-Jui Chang, Changhua County (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/027,379

(22) Filed: Sep. 21, 2020

(65) Prior Publication Data

US 2021/0013399 A1 Jan. 14, 2021

Related U.S. Application Data

(63) Continuation of application No. 15/940,425, filed on Mar. 29, 2018, now Pat. No. 10,784,440.

(Continued)

(51) Int. Cl.
*G11C 11/16* (2006.01)
*H01L 43/08* (2006.01)
(Continued)

(52) U.S. Cl.
CPC .............. *H01L 43/08* (2013.01); *A61K 8/345* (2013.01); *A61K 8/55* (2013.01); *A61K 8/731* (2013.01);
(Continued)

(58) Field of Classification Search
CPC .............................. H01L 43/08; G11C 11/161
See application file for complete search history.

(56) References Cited

U.S. PATENT DOCUMENTS 7,166,881 B2 * 1/2007 Lin .......................... G11C 11/15
257/295
7,692,230 B2 * 4/2010 Liaw .................... G11C 11/1659
257/296
(Continued)

OTHER PUBLICATIONS

Non-Final Office Action issued in related U.S. Appl. No. 15/940,425, dated Mar. 22, 2019.
(Continued)

*Primary Examiner* — Mushfique Siddique
(74) *Attorney, Agent, or Firm* — McDermott Will & Emery LLP

(57) ABSTRACT

A semiconductor device includes a magnetic random access memory (MRAM). The MRAM comprises a plurality of MRAM cells including a first type MRAM cell and a second type MRAM cell. Each of the plurality of MRAM cells includes a magnetic tunneling junction (MTJ) layer including a pinned magnetic layer, a tunneling barrier layer and a free magnetic layer. A size of the MTJ film stack of the first type MRAM cell is different from a size of the MTJ film stack of the second type MRAM cell. In one or more of the foregoing and following embodiments, a width of the MTJ film stack of the first type MRAM cell is different from a width of the MTJ film stack of the second type MRAM cell.

20 Claims, 19 Drawing Sheets

US 11,038,098 B2
Page 2

Related U.S. Application Data

(60) Provisional application No. 62/584,574, filed on Nov. 10, 2017.

(51) Int. Cl.
| | | |
|---|---|---|
| *H01L 43/02* | (2006.01) | |
| *H01L 27/22* | (2006.01) | |
| *H01L 43/10* | (2006.01) | |
| *H01L 43/12* | (2006.01) | |
| *A61K 8/34* | (2006.01) | |
| *A61K 8/55* | (2006.01) | |
| *A61K 8/73* | (2006.01) | |
| *A61K 8/86* | (2006.01) | |
| *A61Q 11/00* | (2006.01) | |

(52) U.S. Cl.
CPC ............... *A61K 8/86* (2013.01); *A61Q 11/00* (2013.01); *G11C 11/161* (2013.01); *H01L 27/228* (2013.01); *H01L 43/02* (2013.01); *H01L 43/10* (2013.01); *H01L 43/12* (2013.01); *G11C 11/1659* (2013.01)

(56) References Cited

U.S. PATENT DOCUMENTS

| | | | |
|---|---|---|---|
| 10,210,920 | B1 | 2/2019 | Chen et al. |
| 10,541,269 | B2* | 1/2020 | Ying ................ H01L 43/12 |
| 2006/0038210 | A1 | 2/2006 | Lin et al. |
| 2010/0019297 | A1 | 1/2010 | Hwang |
| 2013/0001718 | A1* | 1/2013 | Zheng ............ G11C 11/161 |
| | | | 257/421 |
| 2019/0051341 | A1 | 2/2019 | Li et al. |
| 2019/0066746 | A1 | 2/2019 | Li et al. |
| 2019/0165260 | A1* | 5/2019 | Yu ................ H01F 41/308 |
| 2019/0206939 | A1* | 7/2019 | Bozdag ............ G11C 11/00 |

OTHER PUBLICATIONS

Final Office Action issued in related U.S. Appl. No. 15/940,425, dated Aug. 20, 2019.

Non-Final Office Action issued in related U.S. Appl. No. 15/940,425, dated Jan. 31, 2020.

Notice of Allowance issued in related U.S. Appl. No. 15/940,425, dated May 21, 2020.

* cited by examiner

MAGNETIC RANDOM ACCESS MEMORY WITH VARIOUS SIZE MAGNETIC TUNNELING JUNCTION FILM STACKS

RELATED APPLICATION

This application is a continuation application of U.S. patent application Ser. No. 15/940,425 filed on Mar. 29, 2018, which claims priority to U.S. Provisional Application No. 62/584,574 filed on Nov. 10, 2017, the entire contents of each of which are incorporated herein by reference.

TECHNICAL FIELD

The present disclosure relates to a magnetic random access memory (MRAM) device and, more particularly, to a magnetic RAM device based on a magnetic tunnel junction cell formed with a semiconductor device.

BACKGROUND

An MRAM offers comparable performance to volatile static random access memory (SRAM) and comparable density with lower power consumption to volatile dynamic random access memory (DRAM). Compared to non-volatile memory (NVM) flash memory, an MRAM offers much faster access times and suffers minimal degradation over time, whereas a flash memory can only be rewritten a limited number of times. An MRAM cell is formed by a magnetic tunneling junction (MTJ) comprising two ferromagnetic layers which are separated by a thin insulating barrier, and operates by tunneling of electrons between the two ferromagnetic layers through the insulating barrier.

DETAILED DESCRIPTION

It is to be understood that the following disclosure provides many different embodiments, or examples, for implementing different features of the invention. Specific embodiments or examples of components and arrangements are described below to simplify the present disclosure. These are, of course, merely examples and are not intended to be limiting. For example, dimensions of elements are not limited to the disclosed range or values, but may depend upon process conditions and/or desired properties of the device. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity. In the accompanying drawings, some layers/features may be omitted for simplification.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (rotated 90 degrees or at other orientations) and the spatially relative descriptors used herein may likewise be interpreted accordingly. In addition, the term "made of" may mean either "comprising" or "consisting of." Further, in the following fabrication process, there may be one or more additional operations in/between the described operations, and the order of operations may be changed. In the present disclosure, a phrase "one of A, B and C" means "A, B and/or C" (A, B, C, A and B, A and C, B and C, or A, B and C), and does not mean one element from A, one element from B and one element from C, unless otherwise described.

Figure 1B:
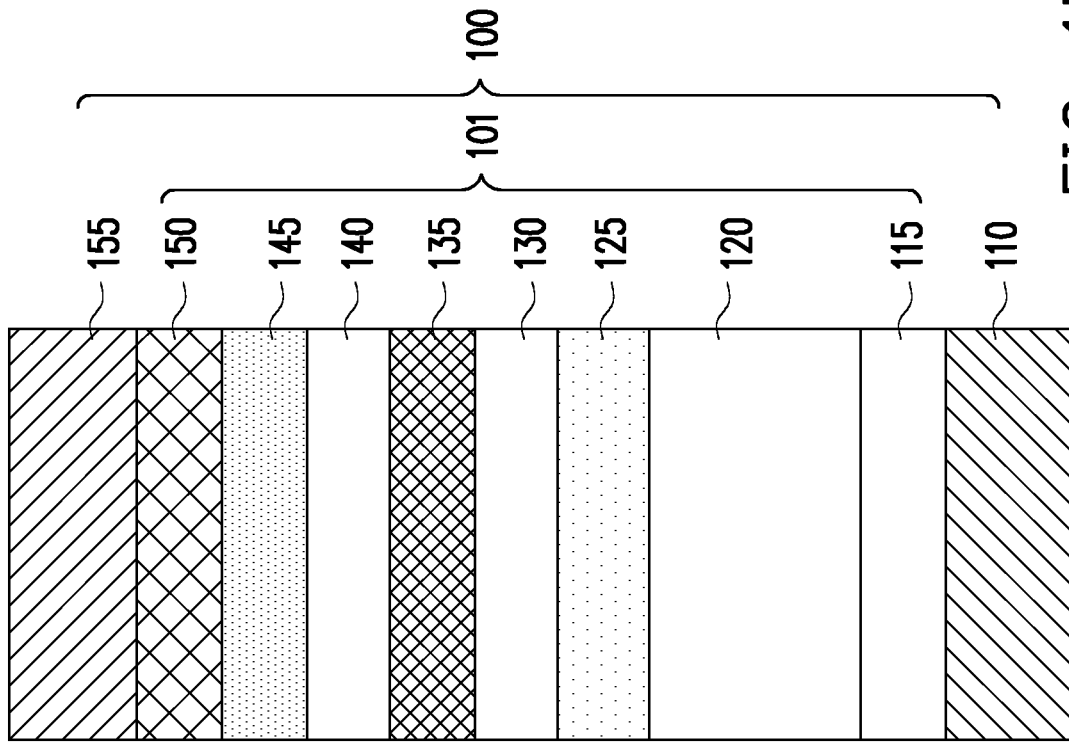
FIG. 1B is a schematic cross sectional view of the MTJ film stack according to an embodiment of the present disclosure.
Figure 1A:
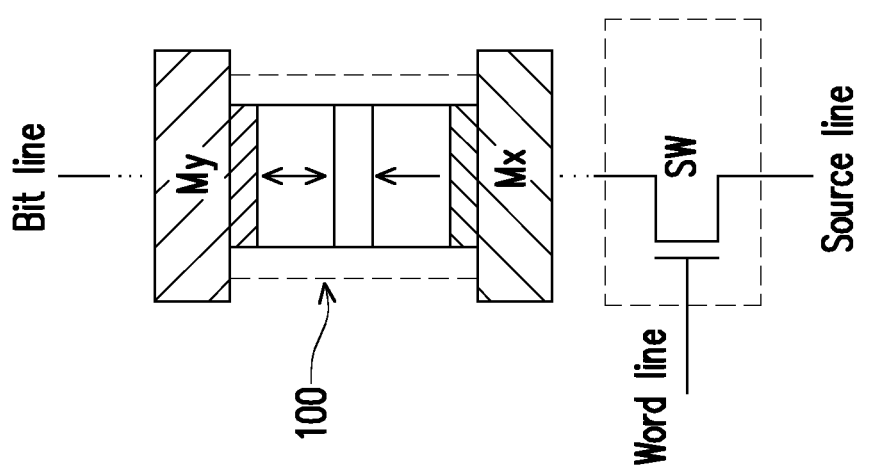
FIG. 1A is a schematic view of a MTJ MRAM cell according to an embodiment of the present disclosure.

FIG. 1A is a schematic view of a MTJ MRAM cell according to an embodiment of the present disclosure, and FIG. 1B is a schematic cross sectional view of the MTJ film stack. The MTJ film stack 100 is disposed between a lower metal layer Mx and an upper metal layer My of a semiconductor device. The metal layers Mx and My are used to connect one element to another element in a semiconductor device formed at a different level above a substrate. Further, the lower metal layer Mx is coupled to a switching device SW, which can be formed by a MOS FET including, but not limited to, a planar MOS FET, a fin FET, a gate-all-around (GAA) FET, or any other switching devices. A control terminal (e.g., a gate terminal of FET) of the switching device is coupled to a word line. The upper metal layer My is coupled to a bit line. In some embodiments, the switching device SW is disposed between the upper metal layer My and the bit line.

The MTJ film stack 100 shown in FIG. 1B includes a first electrode layer 110 coupled to the lower metal layer Mx and a second electrode layer 155 coupled to the upper metal layer My. An MTJ functional layer 101 is disposed between the first electrode layer 110 and the second electrode layer 155.

The MTJ functional layer 101 includes a second pinned magnetic layer 130, a free magnetic layer 140, and a tunneling barrier layer 135 made of a non-magnetic material and disposed between the second pinned magnetic layer 130 and the free magnetic layer 140. The free magnetic layer 140 and the second pinned magnetic layer 130 include one or more ferromagnetic materials that can be magnetically oriented, respectively. The second pinned magnetic layer 130 is configured such that the magnetic orientation is fixed and will not respond to a typical magnetic field. In some embodiments, the thickness of the free magnetic layer 140 is in a range from about 0.8 nm to about 1.5 nm. In some embodiments, the thickness of the second pinned layer 130 is in a range from about 0.8 nm to about 2.0 nm.

The tunneling barrier layer 135 includes a relatively thin oxide layer capable of electrically isolating the free magnetic layer 140 from the second pinned magnetic layer 130 at low potentials and capable of conducting current through electron tunneling at higher potentials. In some embodiments, the tunneling barrier layer 135 is made of magnesium oxide (MgO) having a thickness in a range from about 0.5 nm to about 1.2 nm.

The MTJ functional layer 101 further includes an antiferromagnetic layer 125, as shown in FIG. 1B. The antiferromagnetic layer 125 is used to fix the magnetic orientation of the second pinned magnetic layer 130. The antiferromagnetic layer 125 includes ruthenium (Ru) or any other suitable antiferromagnetic material. In some embodiments, the thickness of the antiferromagnetic layer 125 is in a range from about 0.4 nm to about 1.0 nm.

The MTJ functional layer 101 further includes a first pinned magnetic layer 120 and a second pinned magnetic layer 130 both including one or more magnetic materials, as shown in FIG. 1B. The first electrode layer 110 is formed on the lower metal layer Mx made of, for example, Cu, Al, W, Co, Ni, and/or an alloy thereof, and the upper metal layer My made of, for example, Cu, Al, W, Co, Ni, and/or an alloy thereof, is formed on the second electrode layer 155.

Figure 2C:
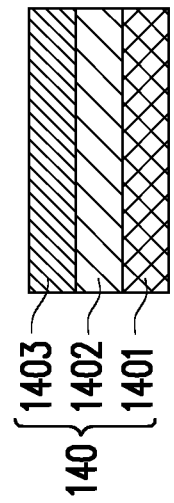
FIGS. 2A, 2B and 2C show schematic cross sectional views of magnetic layers of the MTJ film stack according to an embodiment of the present disclosure.
Figure 2B:
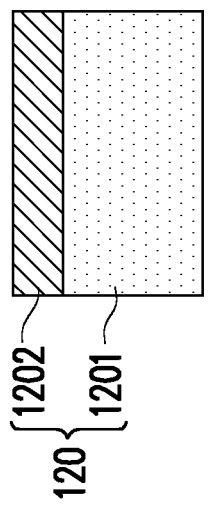
Figure 2A:
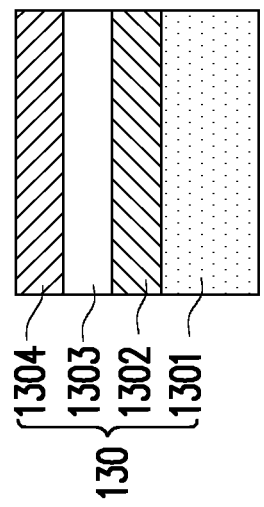

The second pinned magnetic layer 130 includes multiple layers of magnetic materials. In some embodiments, as shown in FIG. 2A, the second pinned magnetic layer 130 includes four layers 1301, 1302, 1303 and 1304, where the layer 1304 is in contact with the tunneling barrier layer 135 and the layer 1301 is in contact with the antiferromagnetic layer 125. In some embodiments, the layer 1301 (the bottommost layer) includes a multilayer structure of cobalt (Co) and platinum (Pt). In some embodiments, a thickness of the cobalt layer is in a range from about 0.3 nm to about 0.6 nm and a thickness of the platinum layer is in a range from about 0.2 nm to about 0.5 nm. The thickness of the cobalt layer can be the same as or greater than the platinum layer. The cobalt layers and the platinum layers are alternately stacked such that the total thickness of the layer 1301 is in a range from about 2.0 nm to about 5.0 nm in some embodiments. The layer 1302 includes a cobalt layer having a thickness in a range from about 0.4 nm to about 0.6 nm. In certain embodiments, the layer 1301 is the cobalt layer and the layer 1302 is the multilayer of the cobalt layers and the platinum layers as set forth above. In this disclosure, an "element" layer generally means that the content of the "element" is more than 99%.

The layer 1303 is a spacer layer. The thickness of the spacer layer 1303 is in a range from about 0.2 nm to about 0.5 nm in some embodiments. The layer 1304 is a cobalt iron boron (CoFeB) layer, a cobalt/palladium (CoPd) layer and/or a cobalt iron (CoFe) layer. The thickness of the layer 1304 is in a range from about 0.8 nm to about 1.5 nm in some embodiments.

The first pinned magnetic layer 120 includes multiple layers of magnetic materials. In some embodiments, as shown in FIG. 2B, the first pinned magnetic layer 120 includes two layers 1201 and 1202, where the layer 1202 is in contact with the antiferromagnetic layer 125. In some embodiments, the layer 1201 includes a multilayer structure of cobalt (Co) and platinum (Pt). In some embodiments, a thickness of the cobalt layer is in a range from about 0.3 nm to about 0.6 nm and a thickness of the platinum layer is in a range from about 0.2 nm to about 0.5 nm. The thickness of the cobalt layer can be the same as or greater than the platinum layer. The cobalt layers and the platinum layers are alternately stacked such that the total thickness of the layer 1301 is in a range from about 5.0 nm to about 10.0 nm in some embodiments. The layer 1302 includes a cobalt layer having a thickness in a range from about 0.4 nm to about 0.6 nm.

The free magnetic layer 140 includes a cobalt iron boron (CoFeB) layer, a cobalt/palladium (CoPd) layer and/or a cobalt iron (CoFe) layer having a thickness in a range from about 1.0 nm to about 2.0 nm in some embodiments. In other embodiments, the free magnetic layer 140 includes multiple layers of magnetic materials. In some embodiments, as shown in FIG. 2C, the free magnetic layer 140 includes three layers 1401, 1402 and 1403, where the layer 1401 is in contact with the tunneling barrier layer 135. The layers 1401 and 1403 are a cobalt iron boron (CoFeB) layer, a cobalt/palladium (CoPd) layer and/or a cobalt iron (CoFe) layer having a thickness in a range from about 1.0 nm to about 2.0 nm in some embodiments. The layer 1402 is a spacer layer. The thickness of the spacer layer 1402 is in a range from about 0.2 nm to about 0.6 nm in some embodiments.

The MTJ functional layer 101 further includes a seed layer 115 formed on the first electrode layer 110, a capping layer 145 formed on the free magnetic layer 140, a diffusion barrier layer 150 formed on the capping layer 145, as shown in FIG. 1B. The capping layer 145 is made of a dielectric material, such as magnesium oxide or aluminum oxide, and has a thickness in a range from about 0.5 nm to about 1.5 nm in some embodiments. The first electrode layer 110 is made of a conductive material, such as a metal (e.g., Ta, Mo, Co, Pt, Ni), to reduce the resistance of the first pinned magnetic layer 120, especially for programming. The second electrode layer 155 is also made of a conductive material, such as a metal, to reduce the resistivity during reading.

The pinned magnetic layer, the free magnetic layer and the antiferromagnetic layer can also be formed by physical vapor deposition (PVD), molecular beam epitaxy (MBE), pulsed laser deposition (PLD), atomic layer deposition (ALD), electron beam (e-beam) epitaxy, chemical vapor deposition (CVD), or derivative CVD processes further comprising low pressure CVD (LPCVD), ultrahigh vacuum CVD (UHVCVD), reduced pressure CVD (RPCVD), or any combinations thereof, or any other suitable film deposition method. The tunneling barrier layer and the diffusion barrier layer can also be formed by CVD, PVD or ALD or any other suitable film deposition method.

FIGS. 3A-3D show a memory operation of MTJ cell. As shown in FIGS. 3A-3D, the MTJ cell includes a pinned magnetic layer 10, a tunneling barrier layer 15 and a free magnetic layer 20. The pinned magnetic layer 10 corresponds to the second pinned magnetic layer 130 or the combination of the first pinned magnetic layer 120, the antiferromagnetic layer 125 and the second pinned magnetic layer 130 of FIG. 1B. The tunneling barrier layer 15 corresponds to the tunneling barrier layer 135 of FIG. 1B and the free magnetic layer 20 corresponds to the free magnetic layer 140 of FIG. 1B. In FIGS. 3A-3D, the remaining layers are omitted. A current source 30 is coupled to the MTJ structure in series.

Figure 3B:
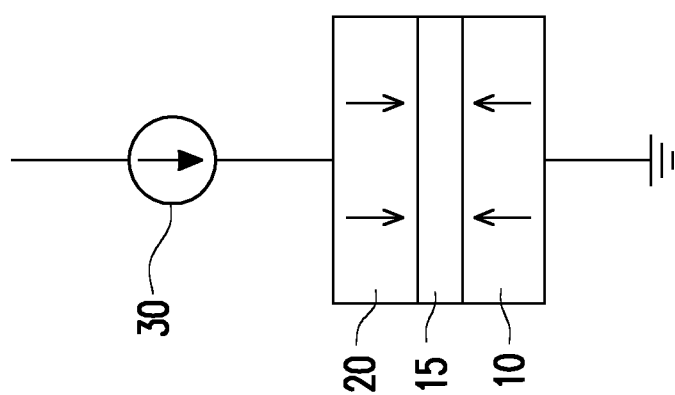
FIGS. 3A and 3B show operations of the MTJ film stack.
Figure 3A:
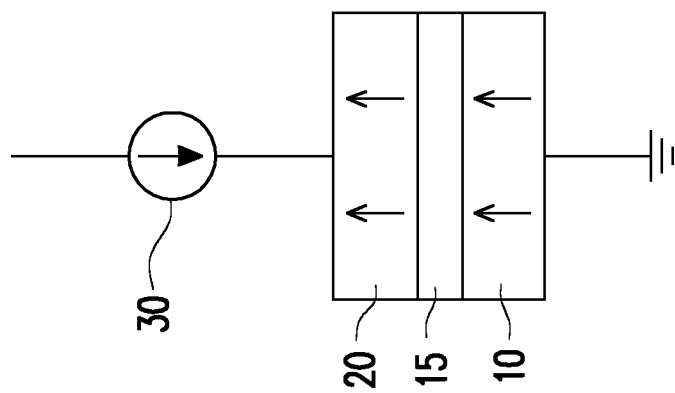
Figure 3C:
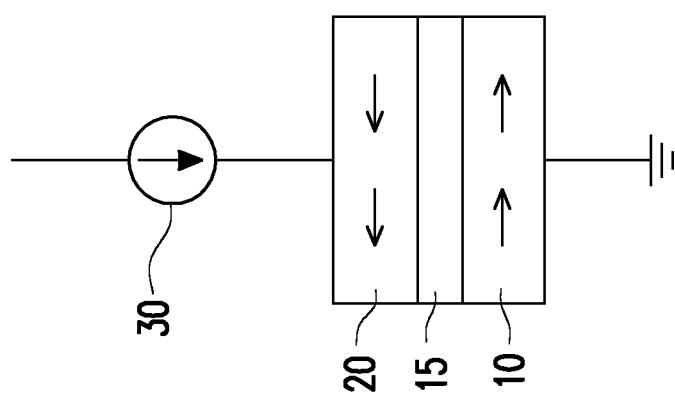
FIGS. 3C and 3D show operations of the MTJ film stack.
Figure 3D:
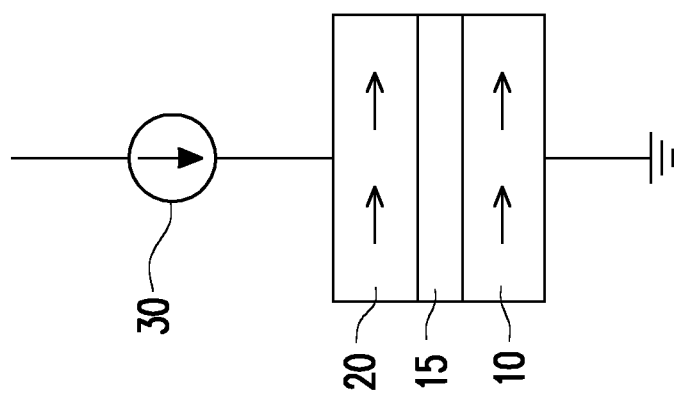

In FIG. 3A, the pinned magnetic layer 10 and the free magnetic layer 20 are magnetically oriented in opposite directions. In some embodiments, the spin directions of the pinned magnetic layer 10 and the free magnetic layer 20 are parallel to the film stack direction (perpendicular to the surface of the films). In FIG. 3B, the pinned magnetic layer 10 and the free magnetic layer 20 are magnetically oriented in the same direction. In other embodiments, the spin directions of the pinned magnetic layer 10 and the free magnetic layer 20 are perpendicular to the film stack direction (parallel with the surface of the films), as shown in FIGS. 3C and 3D. In FIG. 3C, the pinned magnetic layer 10 and the free magnetic layer 20 are magnetically oriented in opposite directions, while in FIG. 3D, the pinned magnetic layer 10 and the free magnetic layer 20 are magnetically oriented in the same direction.

If the same current value $I_C$ is forced to flow through the MTJ cell by the current source 30, it is found that the cell voltage $V_1$ in the case of FIG. 3A (or FIG. 3C) is larger than the cell voltage $V_2$ in the case of FIG. 3B (or FIG. 3D), because the resistance of an opposite-oriented MTJ cell shown in FIG. 3A (or FIG. 3C) is greater than the resistance of a same-oriented MTJ cell shown in FIG. 3B (or FIG. 3D). Binary logic data ("0" and "1") can be stored in a MTJ cell and retrieved based on the cell orientation and resulting resistance. Further, since the stored data does not require a storage energy source, the cell is non-volatile.

Figure 4A:
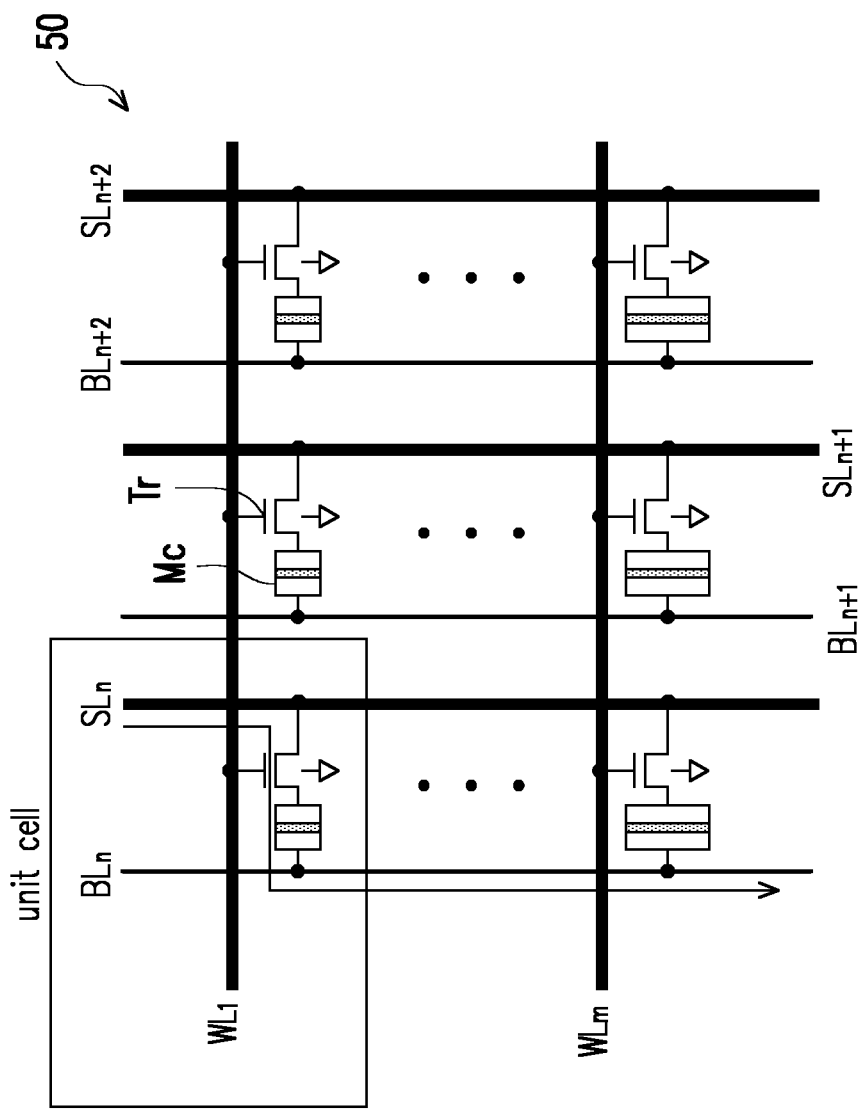
FIG. 4A shows a schematic circuit diagram of an MTJ MRAM.

FIG. 4A shows a schematic circuit diagram of an MTJ MRAM array 50. Each memory cell includes a MTJ cell Mc and a transistor Tr, such as a MOS FET. The gate of the transistor Tr is coupled to one of word lines $WL_1 \ldots WL_m$ and a drain (or a source) of the transistor Tr is coupled to one end of the MTJ cell Mc, and another end of the MTJ cell is coupled to one of bit lines $BL_n$, $BL_{n+1}$ and $BL_{n+2}$. Further, in some embodiments, signal lines (not shown) for programming are provided adjacent to the MTJ cells.

A memory cell is read by asserting the word line of that cell, forcing a reading current through the bit line of that cell, and then measuring the voltage on that bit line. For example, to read the state of a target MTJ cell, the word line is asserted to turn ON the transistor Tr. The free magnetic layer of the target MTJ cell is thereby coupled to one of the fixed potential lines $SL_n$, $SL_{n+1}$ and $SL_{n+2}$, e.g., the ground, through the transistor Tr. Next, the reading current is forced on the bit line. Since only the given reading transistor Tr is turned ON, the reading current flows through the target MTJ cell to the ground. The voltage of the bit line then measured to determine the state ("0" or "1") of the target MTJ cell. In some embodiments, as shown in FIG. 4A, each MTJ cell has one reading transistor Tr. Therefore, this type of MRAM architecture is called 1T1R. In other embodiments, two transistors are assigned to one MTJ cell, forming a 2T1R system. Other cell array configurations can be employed.

Figure 4B:
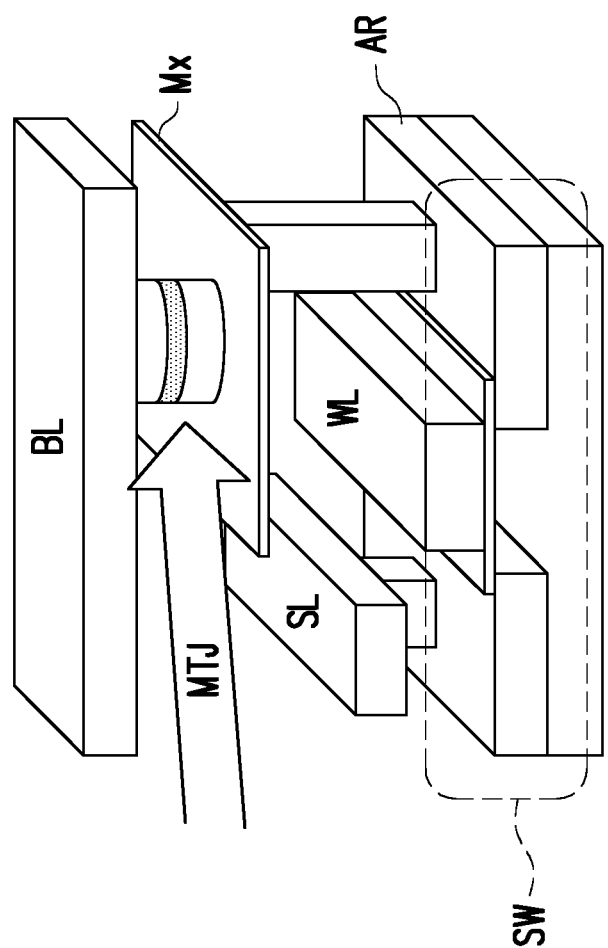
FIG. 4B shows a schematic perspective view of a memory cell of the MTJ MRAM and FIG. 4C shows a memory cell layout of the MTJ MRAM.
Figure 4C:
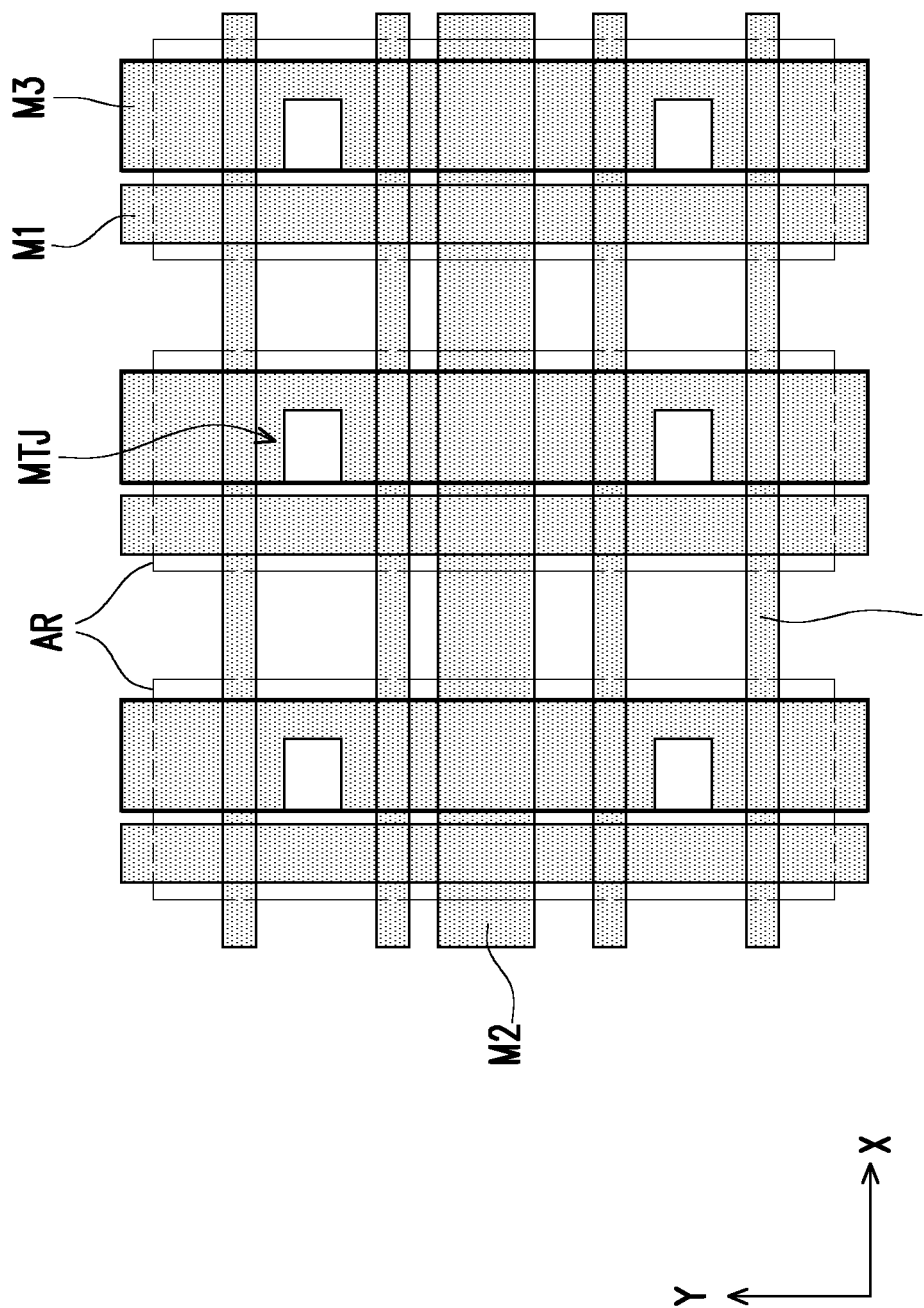

FIG. 4B shows a schematic perspective view of a memory cell of the MTJ MRAM and FIG. 4C shows a memory cell layout of the MTJ MRAM.

As shown in FIGS. 4B and 4C, the MTJ cell MTJ is disposed above a switching device SW, such as a MOS FET. The gate Gate of the MOSFET is a word line WL or coupled to a word line formed by a metal layer. The bottom electrode Mx of the MTJ cell is coupled to a drain of the MOS FET formed in an active region AR and a source of the MOS FET formed in the active region AR is coupled to the source line SL. The upper electrode of the MTJ cell is coupled to a bit line BL. In some embodiments, the source line SL can be formed by metal layers M1 and M2, and the bit line BL can be formed by a metal layer M3. In certain embodiments, one of more metal wirings is a single device layer, and in other embodiments, one or more metal wirings are double or more device layers.

Electrical and/or physical properties of the MTJ MRAM depend upon a size or a volume of the MTJ film stack. For example, read/write speed of the MTJ MRAM is affected by the size or the volume of the MTJ film stack. Generally, when the size or the volume of the MTJ is smaller, the read/write speed becomes faster. In contrast, when the size or the volume of the MTJ is larger, the MTJ film stack is more resistant against thermal processes (larger thermal budget) in the manufacturing process of the MRAM. In the present disclosure, one MRAM device includes multiple MTJ MRAM cells having different MTJ sizes or volumes.

Figure 5A:
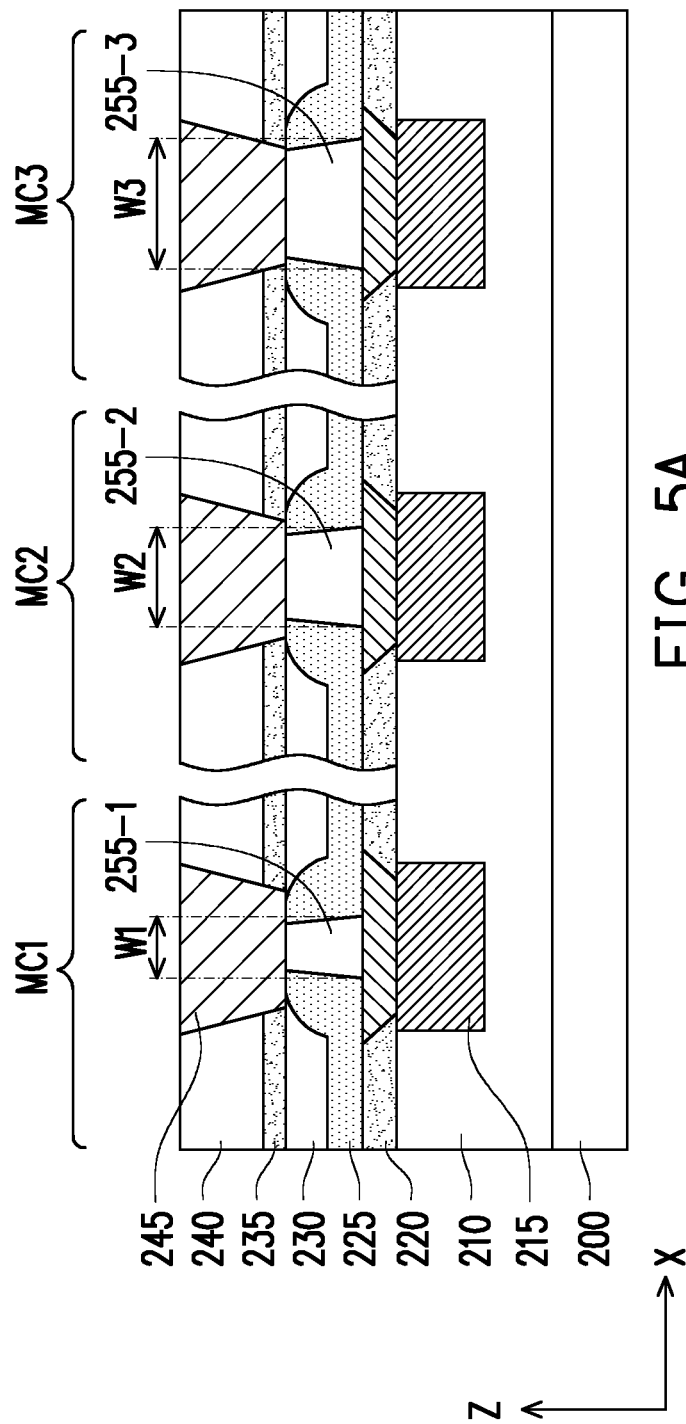
FIG. 5A shows a cross sectional view of a semiconductor device according to an embodiment of the present disclosure.
Figure 5B:
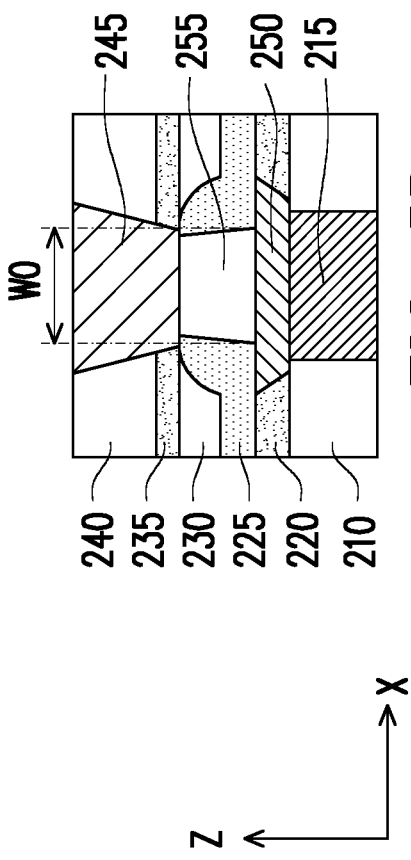
FIG. 5B shows a cross sectional view of an MTJ cell area according to an embodiment of the present disclosure.
Figure 5C:
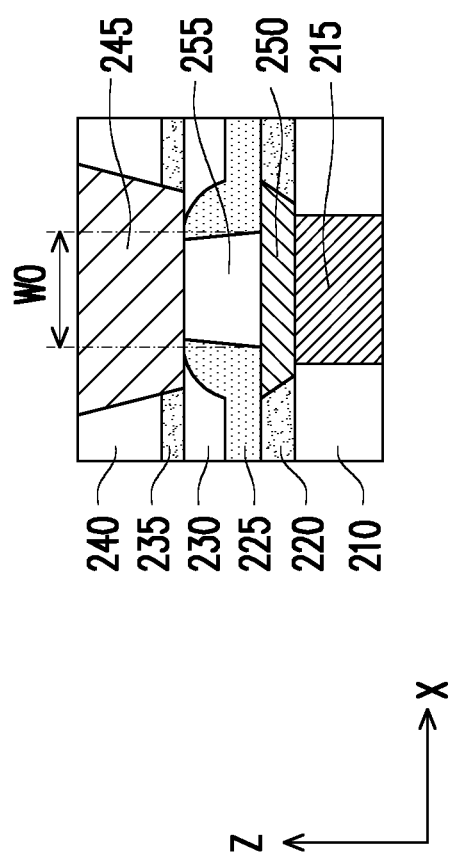
FIG. 5C shows a cross sectional view of an MTJ cell area according to another embodiment of the present disclosure.
Figure 5D:
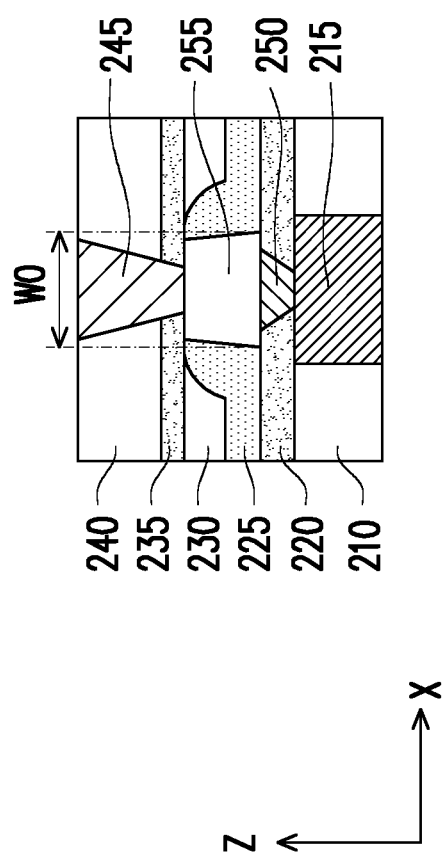
FIG. 5D shows a cross sectional view of an MTJ cell area according to another embodiment of the present disclosure.

FIG. 5A shows a cross sectional view of a MTJ MRAM. FIG. 5B shows an enlarged cross sectional view of the MTJ cell according to an embodiment of the present disclosure, FIG. 5C shows a cross sectional view of an MTJ cell area according to another embodiment of the present disclosure and FIG. 5D shows a cross sectional view of an MTJ cell area according to another embodiment of the present disclosure. Material, configuration, dimensions and/or processes the same as or similar to the foregoing embodiments described with FIGS. 1A-4C may be employed in the following embodiments, and detailed explanation thereof may be omitted.

As shown in FIG. 5A, the MTJ MRAM includes three types of MTJ cells MC1, MC2 and MC3 having different MTJ film stack sizes. The MTJ cells are provided over a substrate 200. In some embodiments, the substrate 200 is made of a suitable elemental semiconductor, such as silicon, diamond or germanium; a suitable alloy or compound semiconductor, such as Group-IV compound semiconductors (silicon germanium (SiGe), silicon carbide (SiC), silicon germanium carbide (SiGeC), GeSn, SiSn, SiGeSn), Group III-V compound semiconductors (e.g., gallium arsenide (GaAs), indium gallium arsenide (InGaAs), indium arsenide (InAs), indium phosphide (InP), indium antimonide (InSb), gallium arsenic phosphide (GaAsP), or gallium indium phosphide (GaInP)), or the like. Further, the substrate 200 may include an epitaxial layer (epi-layer), which may be strained for performance enhancement, and/or may include a silicon-on-insulator (SOI) structure.

Various electronic devices (not shown), such as transistors (e.g., MOS FET), are disposed on the substrate 200. The MOS FET may include planar MOS FET, fin FET and/or gate-all-around FET. A first interlayer dielectric (ILD) layer 210 is disposed over the substrate 200 to cover the electronic devices. The first ILD layer 210 may be referred to as an inter-metal dielectric (IMD) layer. The first ILD layer 210 includes one or more dielectric layers, such as silicon oxide, silicon nitride, silicon oxynitride, fluorine-doped silicate glass (FSG), low-k dielectrics such as carbon doped oxides, extremely low-k dielectrics such as porous carbon doped silicon dioxide, a polymer such as polyimide, combinations of these, or the like. In some embodiments, the first ILD layer 210 is formed through a process such as CVD, flowable CVD (FCVD), or a spin-on-glass process, although any acceptable process may be utilized. Subsequently, a planarization process, such as chemical mechanical polishing (CMP) and/or an etch-back process, or the like is performed.

Further, a lower metal wiring 215 is formed by, for example, a damascene process. The lower metal wiring 215 includes one or more layers of conductive material, such as Cu, a Cu alloy, Al or any other suitable conductive materials.

Each of the MTJ cells MC1, MC2 and MC3 is disposed over the lower metal wiring 215, as shown in FIG. 5A. In the present disclosure, sizes of the MTJ film stack of the MTJ cells MC1, MC2 and MC3 are different from each other. In some embodiments, widths of the MTJ film stack of the MTJ cells MC1, MC2 and MC3 are different from each other. In certain embodiments, thicknesses of the MTJ film stack of the MTJ cells MC1, MC2 and MC3 are the same. Although FIG. 5A shows three different MTJ cells, the number of types of different size MTJ cells is not limited to three. The number of types of different size MTJ cells can be two or more than three.

In some embodiments, the width W2 of the MTJ film 255-2 of the second MTJ cell MC2 is X times or more the width W1 of the MTJ film stack 255-1 of the first MTJ cell MC1, where X is more than one (1.0). In certain embodiments, X is 1.1 or more and in other embodiments, X is 1.2 or more.

In some embodiments, the width W2 of the MTJ film 255-2 of the second MTJ cell MC2 is twice or more the width W1 of the MTJ film stack 255-1 of the first MTJ cell MC1. In other embodiments, the width W2 of the MTJ film stack 255-2 of the second MTJ cell MC2 is three times or more the width W1 of the MTJ film stack 255-1 of the first MTJ cell MC1. In certain embodiments, the width W2 of the MTJ film stack 255-2 of the second MTJ cell MC2 is five times or more the width W1 of the MTJ film stack 255-1 of the first MTJ cell MC1. The widths of the MTJ cells are measured along the X direction in which the gates (word lines) extend, and are defined as a width at the bottom of the MTJ film stack and the bottom electrode.

In some embodiments, the width W2 of the MTJ film stack 255-2 of the second MTJ cell MC2 is fifty times or less, thirty times or less or twenty times or less the width W1 of the MTJ film stack 255-1 of the first MTJ cell MC1.

Similarly, in some embodiments, the width W3 of the MTJ film 255-3 of the third MTJ cell MC3 is Y times or more the width W2 of the MTJ film stack 255-2 of the first MTJ cell MC2, where Y is more than one (1.0). In certain embodiments, Y is 1.1 or more and in other embodiments, Y is 1.2 or more. In some embodiments, the width W3 of the MTJ film stack 255-3 of the third MTJ cell MC3 is twice or more, three times or more or five times or more the width W2 of the MTJ film stack 255-2 of the second MTJ cell MC2, and the width W3 of the MTJ film stack 255-3 of the third MTJ cell MC3 is fifty times or less, thirty times or less or twenty times or less the width W2 of the MTJ film stack 255-2 of the second MTJ cell MC2.

In some embodiments, the width W1 of the MTJ film stack 255-1 of the first MTJ cell MC1 is in a range from about 10 nm to about 50 nm, the width W2 of the MTJ film stack 255-2 of the second MTJ cell MC2 is in a range from about 100 nm to about 500 nm and the width W3 of the MTJ film stack 255-3 of the third MTJ cell MC3 is in a range from about 1000 nm to about 5000 nm.

In other embodiments, the difference in the widths of the MTJ film stack is in a range from about 10 nm to about 100 nm.

In some embodiments, a plurality of the first MTJ cells MC1 constitute a first MRAM including driver circuits, a plurality of the second MTJ cells MC2 constitute a second MRAM including driver circuits, and a plurality of the third MTJ cells MC3 constitute a third MRAM including driver circuits.

As shown in FIG. 5B, each of the MTJ cells and the structure therearound has substantially the same structure except for the size (width). A first etch stop layer 220 is formed on the first ILD layer 210. In some embodiments, the first etch stop layer 220 includes a material different from the first ILD layer 210 and includes silicon carbide, silicon nitride, aluminum oxide or any other suitable material in some embodiments.

A bottom electrode 250 is formed in contact with the lower metal wiring 215 and embedded in the first etch stop layer 220 in some embodiments. The bottom electrode 250 is similar to the first electrode layer 110 shown in FIGS. 1A and 1s made of, for example, TiN, Ta, Mo, Co, Pt, Ni, and/or an alloy thereof.

An MTJ film stack 255 is formed on the bottom electrode 250 as shown in FIGS. 5A and 5B. The MTJ film stack 255 corresponds to the MTJ functional layer 101 of FIG. 1B. The width W0 of the MTJ cell is measured at the interface between the bottom electrode 250 and the bottom-most layer of the MTJ film stack 255, which is the first pinned layer 120. If a seed layer 115 is used, the width W0 of the MTJ cell is measured at the interface between the bottom electrode 250 and the seed layer 115.

In some embodiments, a sidewall spacer layer 225 is formed on opposing side walls of the MTJ film stack 255. The sidewall spacer layer 225 includes one or more layers of insulating material, such as silicon oxide, silicon nitride, SiON, SiCN or any other suitable material.

Further a second ILD layer 230 is formed and a planarization operation is performed to expose the upper surface of the MTJ film stack 255. The second ILD layer 230 includes one or more dielectric layers, such as silicon oxide, silicon nitride, silicon oxynitride, fluorine-doped silicate glass (FSG), low-k dielectrics such as carbon doped oxides, extremely low-k dielectrics such as porous carbon doped silicon dioxide, a polymer such as polyimide, combinations of these, or the like.

Further, a second etch stop layer 235 is formed on the second ILD layer 230. In some embodiments, the second etch stop layer 235 includes a material different from the second ILD layer 230 and includes silicon carbide, silicon nitride, aluminum oxide or any other suitable bacterial in some embodiments. A third ILD layer 240 is formed over the second etch stop layer 235. The third ILD layer 240 includes one or more dielectric layers, such as silicon oxide, silicon nitride, silicon oxynitride, fluorine-doped silicate glass (FSG), low-k dielectrics such as carbon doped oxides, extremely low-k dielectrics such as porous carbon doped silicon dioxide, a polymer such as polyimide, combinations of these, or the like. An upper electrode 245 is formed in contact with the MTJ film stack 255, as shown in FIG. 5B. The upper electrode 245 is similar to the second electrode layer 155 shown in FIGS. 1A and 1s made of, for example, TiN, Ta, Mo, Co, Pt, Ni, and/or an alloy thereof.

In some embodiments, when the size (width) of the upper electrode 245 is relatively small as shown in FIG. 5B, the upper electrode 245 partially penetrates the sidewall spacer layer 225. When the size (width) of the upper electrode 245 is relatively large as shown in FIG. 5C, the bottom of the upper electrode 245 is disposed over the sidewall spacer layer 225. In other embodiments, the size (width) of the upper electrode 245 is smaller than the upper surface of the MTJ film stack 255, as shown in FIG. 5D. Further, in certain embodiments, the size (width) of the bottom electrode 250 is smaller than the bottom surface of the MTJ film stack 255, as shown FIG. 5D. The smaller bottom electrode 250 of FIG. 5D can be applied to the structures of FIGS. 5B and 5C. In some embodiments, the upper electrode 245 slightly penetrates into the MTL film stack 255.

Further, in some embodiments, the lower metal wiring 215 acts as the first electrode layer 110 of FIGS. 1B and 1n such a case, the bottom electrode 250 is omitted.

Figure 6:
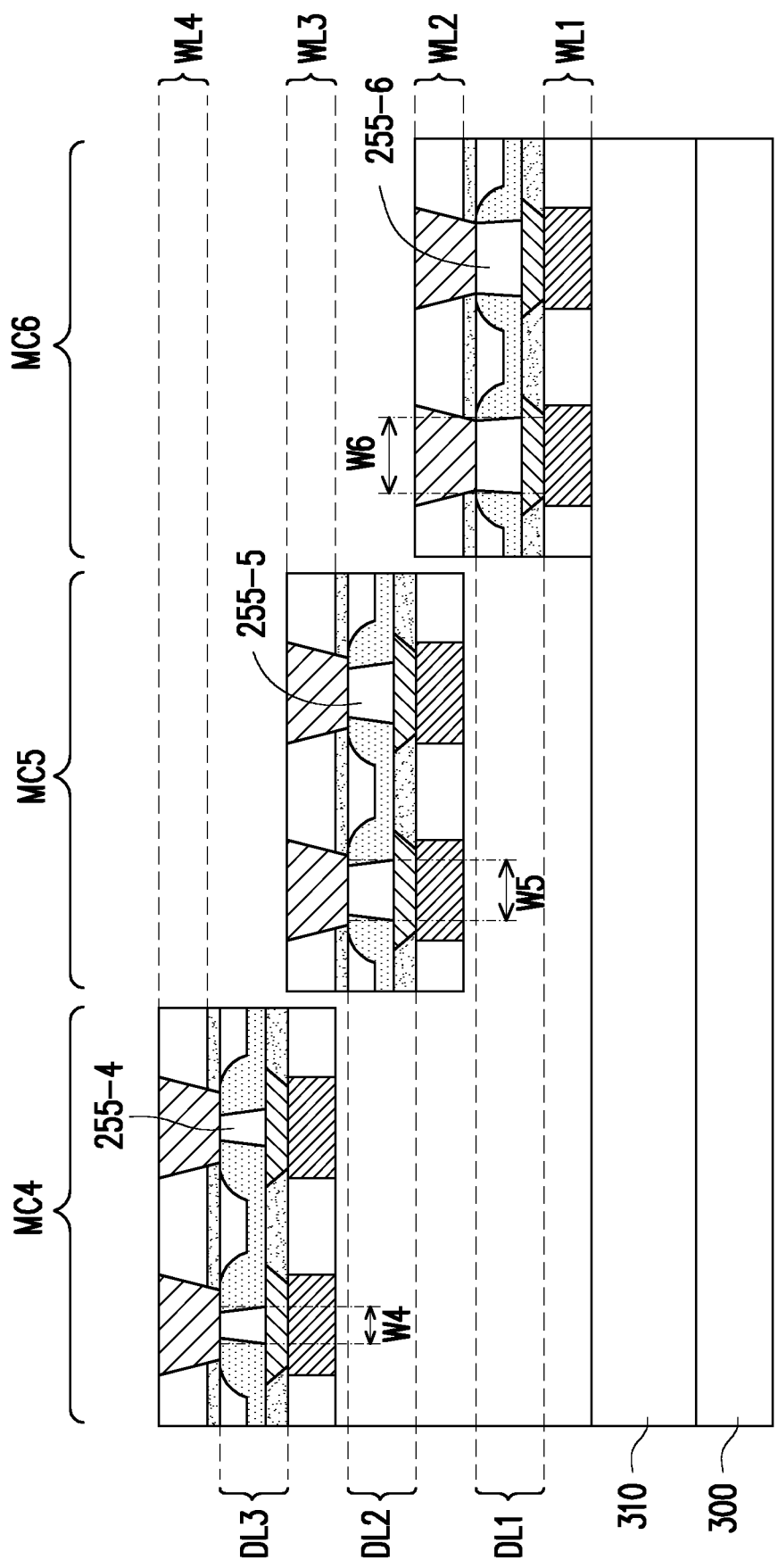
FIG. 6 shows a cross sectional view of a semiconductor device according to another embodiment of the present disclosure.

FIG. 6 shows an MTJ MRAM according to another embodiment of the present disclosure. Materials, configurations, dimensions and/or processes the same as or similar to the foregoing embodiments described with FIGS. 1A-5B may be employed in the following embodiments, and detailed explanation thereof may be omitted. In the foregoing embodiments shown in FIG. 5A, the three different types of MTJ cells having different widths are disposed in the same device layer. The device layer here means a layer between one metal wiring layer and the next metal wiring layer disposed above the one metal wiring layer in the vertical direction. In the embodiment of FIG. 6, different types of the MTJ cells are disposed in different device layers having different levels from the substrate.

In some embodiments, a fourth MTJ cell MC4 is disposed in a third device layer DL3 between a third wiring layer WL3 and a fourth wiring layer WL4, a fifth MTJ cell MC5 is disposed in a second device layer DL2 between the third wiring layer WL3 and a second wiring layer WL2, and a sixth MTJ cell MC6 is disposed in the first device layer DL1 between the second wiring layer WL2 and a first wiring layer WL1. The wiring layers WL1-WL4 are disposed in this order from the substrate 300. In FIG. 6, an ILD layer 310 is formed over the substrate 300 and the MTJ cell MC6 is disposed on the ILD layer 310. However, in other embodiments, one or more other ILD layers are disposed between the ILD layer 310 and the MTJ call MC6.

In some embodiments, one or more wiring layers and one or more ILD layers are disposed between the first device layer DL1 and the second device layer DL2 and/or between the second device layer DL2 and the third device layer DL3.

The sizes of the MTJ film stacks of the fourth MTJ cell MC4, the fifth MTJ cell MC5 and the sixth MTJ cell MC6 may be the same or may be different from each other.

In some embodiments, the width W4 of the MTJ film stack 255-4 of the fourth MTJ cell MC4 is smaller than the width W5 of the MTJ film stack 255-5 of the fifth MTJ cell MC5, and the width W5 of the MTJ film stack 255-5 of the fifth MTJ cell MC5 is smaller than the width W6 of the MTJ film stack 255-6 of the sixth MTJ cell MC6.

In some embodiments, the width W5 of the MTJ film stack 255-5 of the fifth MTJ cell MC5 is twice or more, three times or more or five times or more the width W4 of the MTJ film stack 255-4 of the fourth MTJ cell MC4, and the width W6 of the MTJ film stack 255-6 of the sixth MTJ cell MC6 is twice or more, three times or more or five times or more the width W5 of the MTJ film stack 255-5 of the fifth MTJ cell MC5. In some embodiments, the width W5 of the MTJ film stack 255-5 of the fifth MTJ cell MC5 is fifty times or less, thirty times or less or twenty times or less the width W4 of the MTJ film stack 255-4 of the fourth MTJ cell MC4, and the width W6 of the MTJ film stack 255-6 of the sixth MTJ cell MC6 is fifty times or less, thirty times or less or twenty times or less the width W5 of the MTJ film stack 255-5 of the fifth MTJ cell MC5.

In some embodiments, the width W4 of the MTJ film stack 255-4 of the fourth MTJ cell MC4 is in a range from about 10 nm to about 50 nm, the width W5 of the MTJ film stack 255-5 of the fifth MTJ cell MC5 is in a range from about 100 nm to about 500 nm and the width W6 of the MTJ film stack 255-6 of the sixth MTJ cell MC3 is in a range from about 1000 nm to about 5000 nm. The thicknesses of MTJ film stacks of the fourth, fifth and sixth MTJ cells may be the same or different from each other.

In some embodiments, a plurality of the fourth MTJ cells MC4 constitute a first MRAM including driver circuits, a plurality of the fifth MTJ cells MC5 constitute a second MRAM including driver circuits, and a plurality of the sixth MTJ cells MC6 constitute a third MRAM including driver circuits.

Devices disposed in the lower device layer may undergo more thermal processes than the devices disposed in the upper device layer. Accordingly, it is beneficial to place larger size MTJ cells, which have a relatively higher thermal budget, in the lower device layer.

In other embodiments, MTJ cells having a smaller size are disposed in the lower device layer. In some embodiments, the same type (same size) of the MTJ cells are disposed in different device layers having different levels from the substrate. In certain embodiments, smallest size MTJ cells or largest size MTJ cells can be disposed at any device layer.

Figure 7:
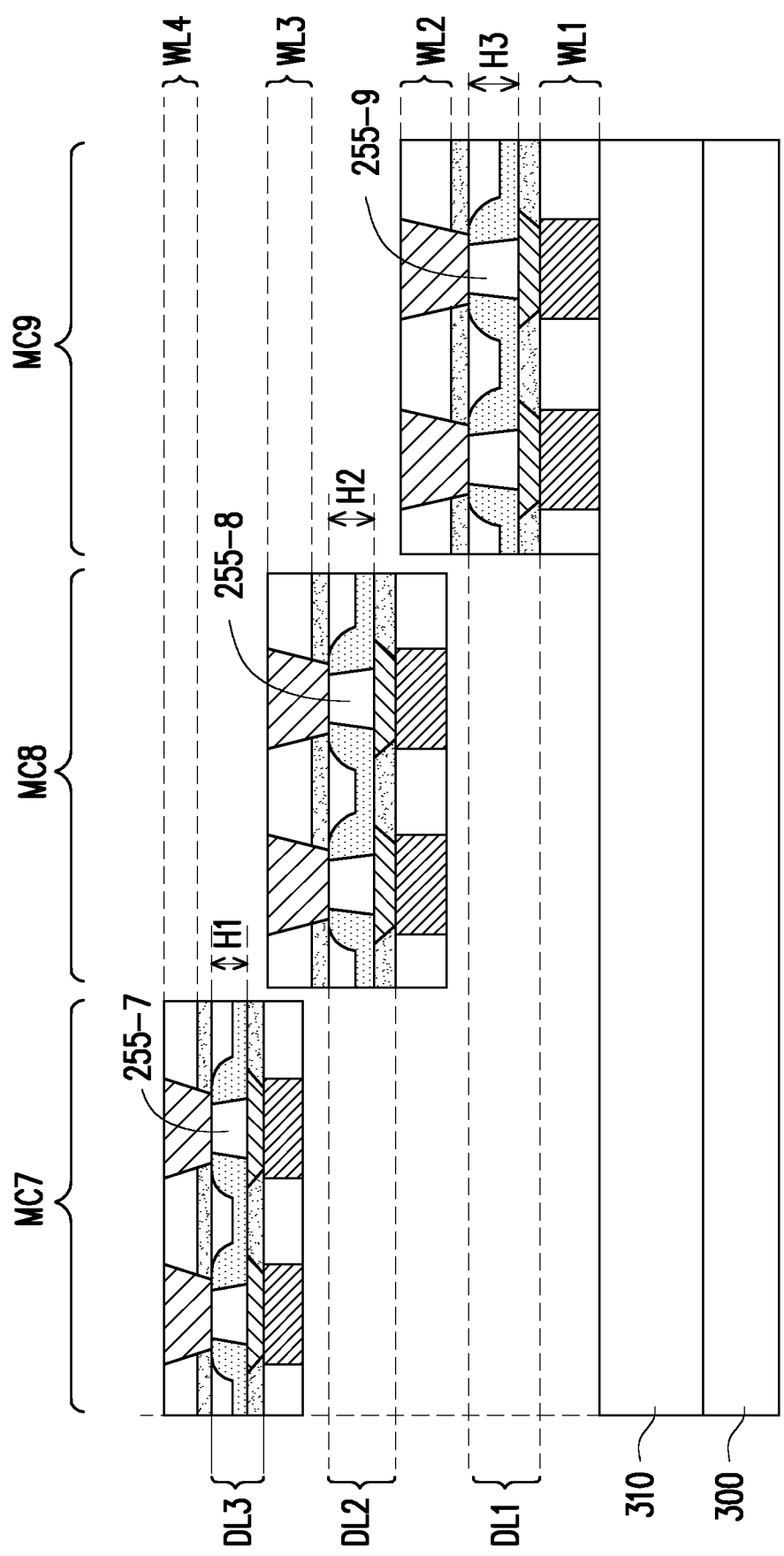
FIG. 7 shows a cross sectional view of a semiconductor device according to another embodiment of the present disclosure.

FIG. 7 shows an MTJ MRAM according to another embodiment of the present disclosure. Materials, configurations, dimensions and/or processes the same as or similar to the foregoing embodiments described with FIGS. 1A-6 may be employed in the following embodiments, and detailed explanation thereof may be omitted. In the foregoing embodiments shown in FIGS. 5A and 6, the three different types of MTJ cells having different widths. In the embodiment of FIG. 7, different types of the MTJ cells having different MTJ film stack thicknesses are disposed in different device layers having different levels from the substrate.

In some embodiments, a seventh MTJ cell MC7 is disposed in a third device layer DL3 between a third wiring layer WL3 and a fourth wiring layer WL4, an eighth MTJ cell MC8 is disposed in a second device layer DL2 between the third wiring layer WL3 and a second wiring layer WL2, and a ninth MTJ cell MC9 is disposed in the first device layer DL1 between the second wiring layer WL2 and a first wiring layer WL1. The wiring layers WL1-WL4 are disposed in this order from the substrate 300. In some embodiments, one or more wiring layers and one or more ILD layers are disposed between the first device layer DL1 and the second device layer DL2 and/or between the second device layer DL2 and the third device layer DL3.

In some embodiments, the thickness H1 of the MTJ film stack of the seventh MTJ cell MC7 is smaller than the thickness H2 of the MTJ film stack of the eighth MTJ cell MC8, and the thickness H2 of the MTJ film stack of the eighth MTJ cell MC8 is smaller than the thickness of the MTJ film stack of the ninth MTJ cell MC9.

In some embodiments, the thickness H2 of the MTJ film stack 255-8 of the eighth MTJ cell MC8 is 1.1 times of more, 1.2 times or more, twice or more, three times or more or five times or more the thickness H1 of the MTJ film stack 255-7 of the seventh MTJ cell MC7, and the thickness H3 of the MTJ film stack 255-9 of the ninth MTJ cell MC9 is 1.1 times of more, 1.2 times or more, twice or more, three times or more or five times or more the thickness H2 of the MTJ film stack 255-8 of the eighth MTJ cell MC8. In some embodiments, the thickness H2 of the MTJ film stack 255-8 of the eighth MTJ cell MC8 is fifty times or less, twenty times or less, ten times or less, five times or less or twice or less the thickness H1 of the MTJ film stack 255-7 of the seventh MTJ cell MC7, and the thickness H3 of the MTJ film stack 255-9 of the ninth MTJ cell MC9 is fifty times or less, twenty times or less, ten times or less, five times or less or twice or less the thickness H2 of the MTJ film stack 255-8 of the eighth MTJ cell MC8.

In some embodiments, the thickness H1 of the MTJ film stack 255-7 of the seventh MTJ cell MC7 is in a range from about 10 nm to about 50 nm, the thickness H2 of the MTJ film stack 255-8 of the eighth MTJ cell MC8 is in a range from about 100 nm to about 500 nm and the thickness H3 of the MTJ film stack 255-9 of the ninth MTJ cell MC3 is in a range from about 1000 nm to about 5000 nm. The widths of the MTJ film stacks of the seventh, eighth and ninth MTJ cells may be the same or different from each other.

In some embodiments, a plurality of the seventh MTJ cells MC7 constitute a first MRAM including driver circuits, a plurality of the eighth MTJ cells MC8 constitute a second MRAM including driver circuits, and a plurality of the ninth MTJ cells MC9 constitute a third MRAM including driver circuits.

Devices disposed in the lower device layer may undergo more thermal processes than the devices disposed in the upper device layer. Accordingly, it is beneficial to place larger size MTJ cells, which have a relatively higher thermal budget, in the lower device layer. In other embodiments, MTJ cells having a smaller size are disposed in the lower device layer.

The embodiments shown in FIGS. 6 and 7 can be combined. In other words, the MTJ film stacks disposed on different device layer can have different width and different thickness.

FIGS. 8A-8G shows various stage of a sequential manufacturing process of the MRAM device according to an embodiment of the present disclosure. It is understood that additional operations can be provided before, during, and after processes shown by FIGS. 8A-8G, and some of the operations described below can be replaced or eliminated, for additional embodiments of the method. The order of the operations/processes may be interchangeable. Material, configuration, dimensions and/or processes the same as or similar to the foregoing embodiments described with respect to FIGS. 1A-7 may be employed in the following embodiments, and detailed explanation thereof may be omitted.

Figure 8A:
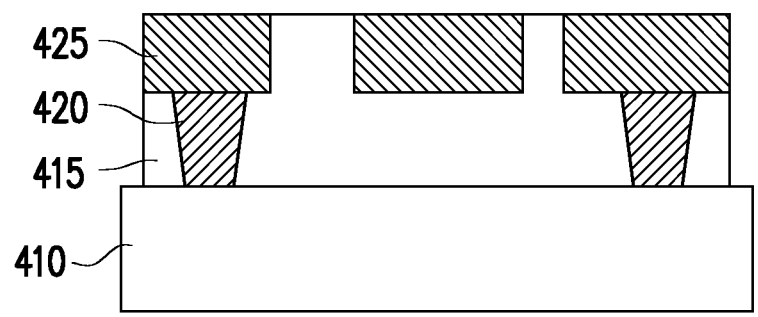
FIGS. 8A, 8B, 8C, 8D, 8E, 8F and 8G show various stages of a sequential manufacturing process of the MRAM device according to an embodiment of the present disclosure.

As shown in FIG. 8A, a second ILD layer 415 is formed over a first ILD layer 410, and a first contact plug 420 and a first metal wiring 425 are formed in the second ILD layer 420. The first and second ILD layers are made of one or more dielectric layers, such as silicon oxide, silicon nitride, silicon oxynitride, fluorine-doped silicate glass (FSG), low-k dielectrics such as carbon doped oxides, extremely low-k dielectrics such as porous carbon doped silicon dioxide, a polymer such as polyimide, combinations of these, or the like. In some embodiments, an etch stop layer is formed between the first ILD layer 410 and the second ILD layer 415. The first contact plug 420 includes one or more metallic materials, such as Cu, Al, AlCu, W, Co, TiN, Ti, Ta and any other suitable conductive materials. The first metal wiring 425 corresponds to the lower metal layer Mx of FIG. 1A and/or the lower metal wiring 215 of FIG. 5B, and includes one or more layers of conductive material, such as Cu, a Cu alloy, Al or any other suitable conductive materials.

Figure 8B:
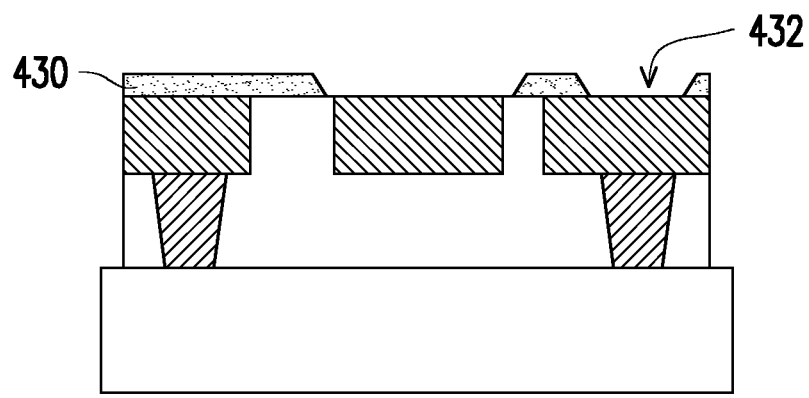

Further, as shown in FIG. 8B, an additional ILD layer or an etch stop layer 430 is formed over the second ILD layer and the first metal wiring 425, and then a contact hole 432 is formed over the first metal wiring 425.

Figure 8C:
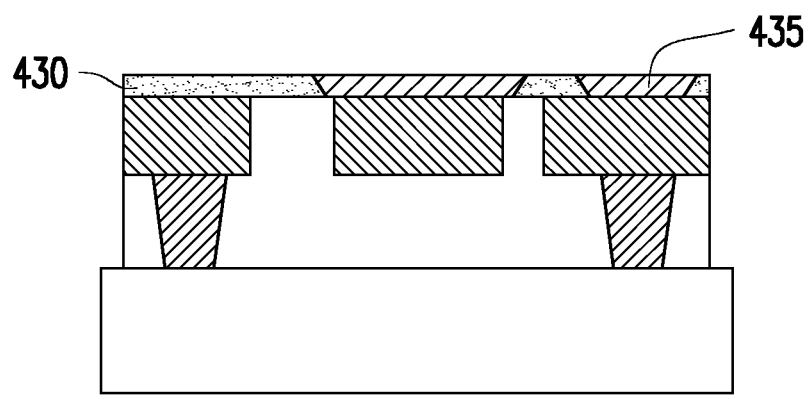

As shown in FIG. 8C, the contact hole 432 is filled with a conductive material so as to form a lower electrode 435. The lower electrode 435 corresponds to the first electrode layer 110 of FIG. 1B and/or the bottom electrode 250 of FIG. 5B, and includes a conductive material, such as a metal (e.g., Ta, Mo, Co, Pt, Ni). When the height of the MTJ stack is small, the lower electrode 435 is utilized to adjust the entire height of the MTJ stack. In some embodiments, the first metal wiring 425 acts as the first electrode layer 110 of FIGS. 1B and 1n such a case, the lower electrode 435 is omitted.

Figure 8D:
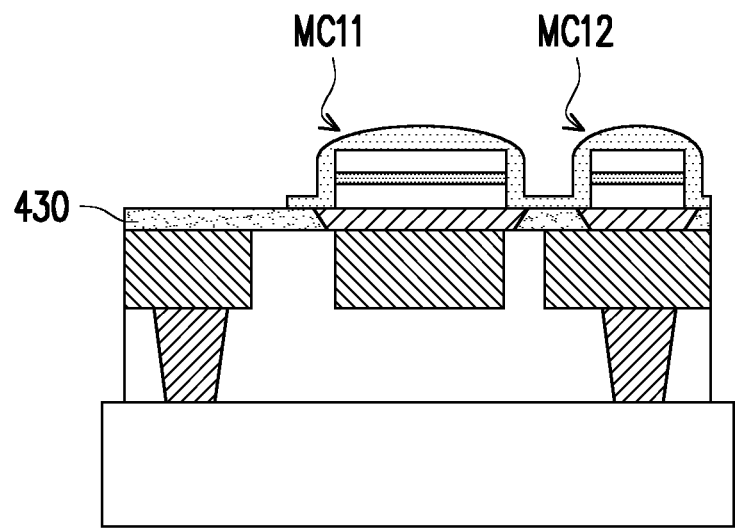

Subsequently, an MTJ film stack MC11 and an MTJ film stack MC12 are formed over the lower electrodes 435, as shown in FIG. 8D. The MTJ film stack MC11 has a larger width than the MTJ film stack MC12. The MTJ film stacks can be formed by depositing multiple layers for the MTJ film stack, and performing one or more lithography and etching operations. The MTJ film stacks are covered by a sidewall spacer layer similar to the sidewall spacer layer 225 of FIG. 5B.

Figure 8E:
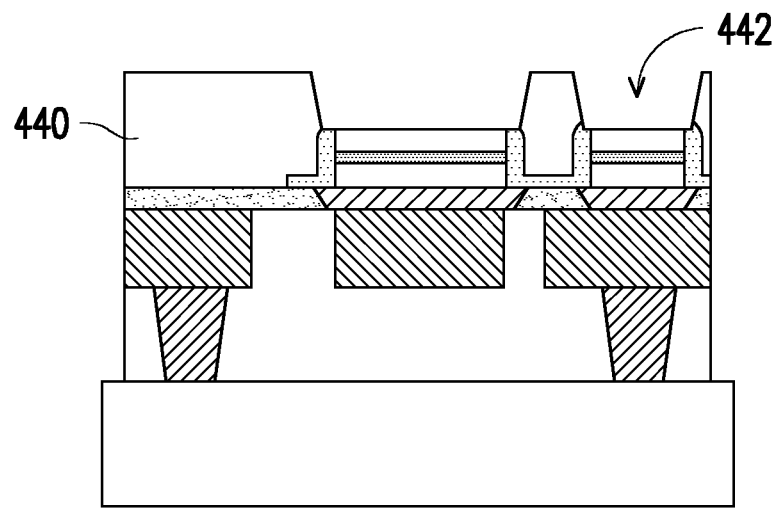

Then, as shown in FIG. 8E, a third ILD layer 440 is formed over the MTJ film stacks, and then a contact hole 442 is formed over the MTJ film stacks MC11 and MC12. The material of the third ILD layer 440 is the same as or similar to that of the first and/or second ILD layers 410, 415.

Figure 8F:
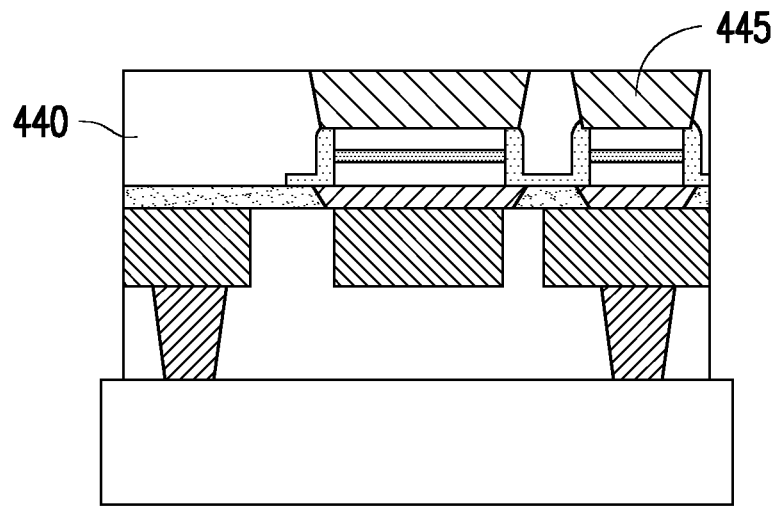
Figure 8G:
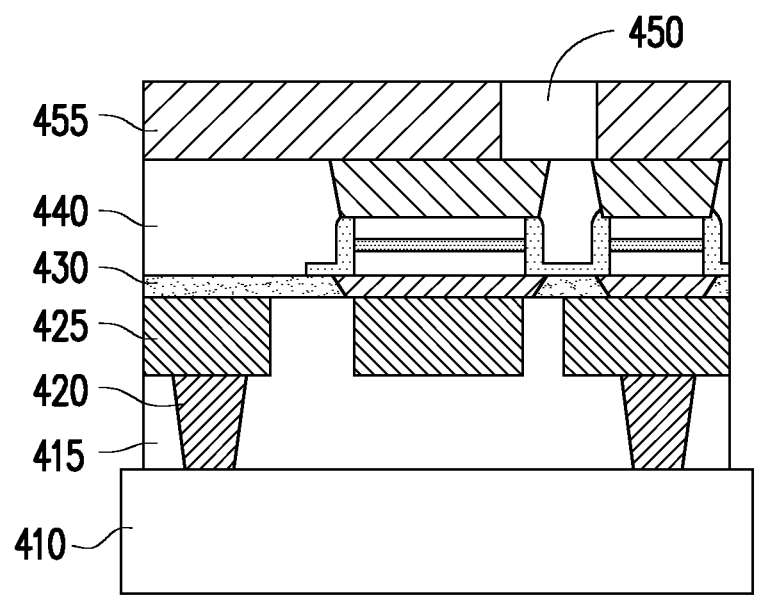

As shown in FIG. 8F, the contact hole 442 is filled with a conductive material so as to form an upper electrode 445. The upper electrode 445 corresponds to the second electrode layer 155 of FIG. 1B and/or the upper electrode 245 of FIG. 5B, and includes a conductive material, such as a metal (e.g., Ta, Mo, Co, Pt, Ni). Then, as shown in FIG. 8G, a fourth ILD layer 450 is formed over the third ILD layer 440 and a second metal wiring 455 is formed on the upper electrode 445. The material of the fourth ILD layer 450 is the same as or similar to that of the first, second and/or third ILD layers. The second metal wiring 455 corresponds to the upper metal layer My of FIG. 1A and/or the upper metal wiring 245 of FIG. 5B, and includes one or more layers of conductive material, such as Cu, a Cu alloy, Al or any other suitable conductive materials. In some embodiments, the second metal wiring 455 acts as the second electrode layer 155 of FIGS. 1B and 1n such a case, the upper electrode 445 is omitted.

FIGS. 9A-9I shows various stage of a sequential manufacturing process of the MRAM device according to an embodiment of the present disclosure. It is understood that additional operations can be provided before, during, and after processes shown by FIGS. 9A-9I, and some of the operations described below can be replaced or eliminated, for additional embodiments of the method. The order of the operations/processes may be interchangeable. Materials, configurations, dimensions and/or processes the same as or similar to the foregoing embodiments described with respect to FIGS. 1A-8G may be employed in the following embodiments, and detailed explanation thereof may be omitted.

Figure 9A:
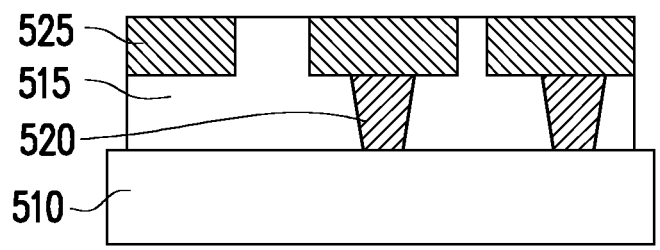
FIGS. 9A, 9B, 9C, 9D, 9E, 9F, 9G, 9H and 9I show various stages of a sequential manufacturing process of the MRAM device according to another embodiment of the present disclosure.

As shown in FIG. 9A, a second ILD layer 515 is formed over a first ILD layer 510, and a first contact plug 520 and a first metal wiring 525 are formed in the second ILD layer 520, similar to FIG. 8A.

Figure 9B:
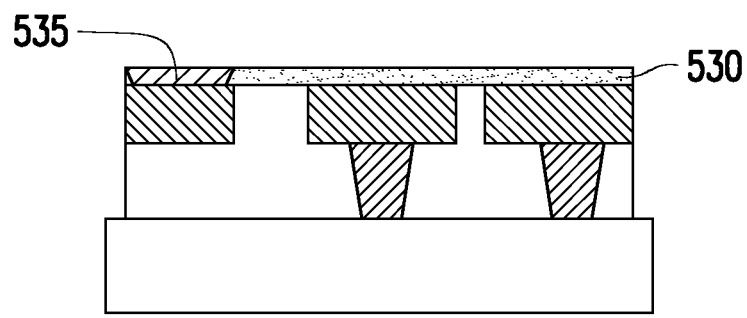

Further, as shown in FIG. 9B, an additional ILD layer or an etch stop layer 530 is formed over the second ILD layer 515 and the first metal wiring 525, and then a contact hole is formed over the first metal wiring 525, similar to FIG. 8B, and further, the contact hole is filled with a conductive material so as to form a first lower electrode 535, similar to FIG. 8C.

Figure 9C:
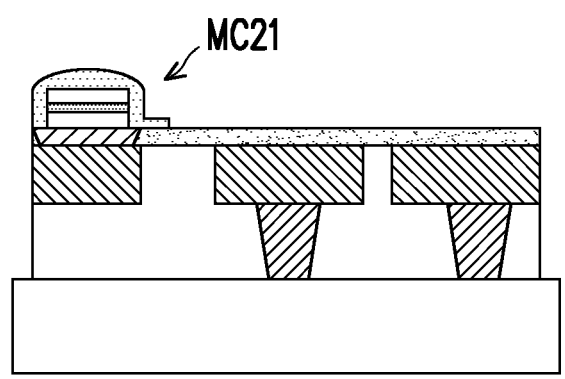
Figure 9D:
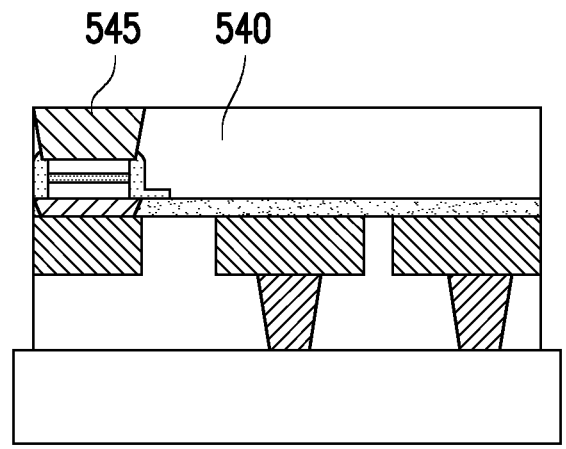

Subsequently, an MTJ film stack MC21 is formed over the first lower electrodes 535, as shown in FIG. 9C, similar to FIG. 8D. Then, similar to FIGS. 8E and 8F, a third ILD layer 540 is formed over the MTJ film stack MC21, and a first upper electrode 545 is formed as shown in FIG. 9D.

Figure 9E:
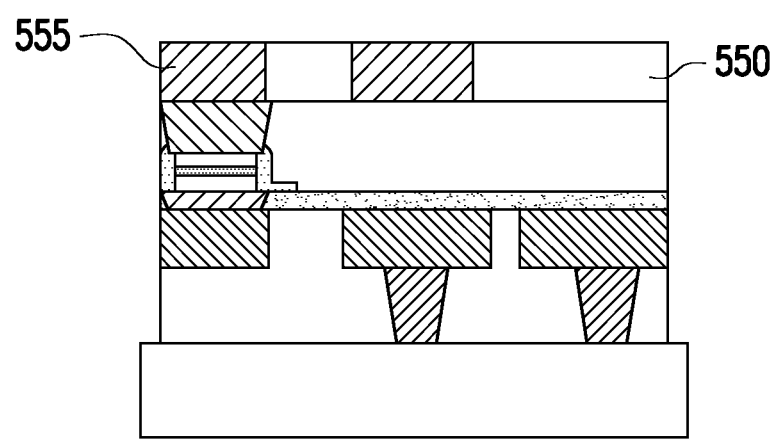

Then, similar to FIG. 8G, a fourth ILD layer 550 is formed over the third ILD layer 540 and a second metal wiring 555 is formed, as shown in FIG. 9E.

Further, by similar operations explained with reference to FIGS. 9B-9C, an additional ILD layer or an etch stop layer 557 is formed over the fourth ILD layer 550, and a second lower electrode 559 is formed. Then, an MTJ film stack MC22 is formed. A fifth ILD layer 560 is formed to cover the MTJ film stack MC22 and a second upper electrode 565 is formed, as shown in FIG. 9F.

Figure 9F:
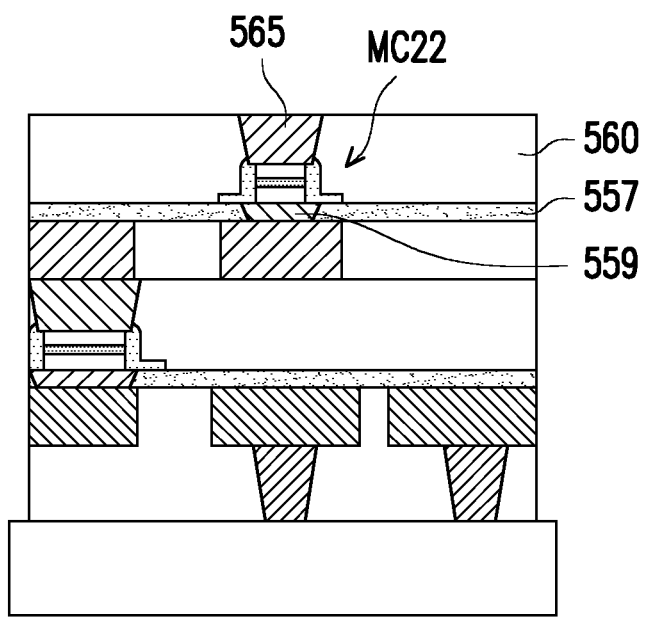
Figure 9G:
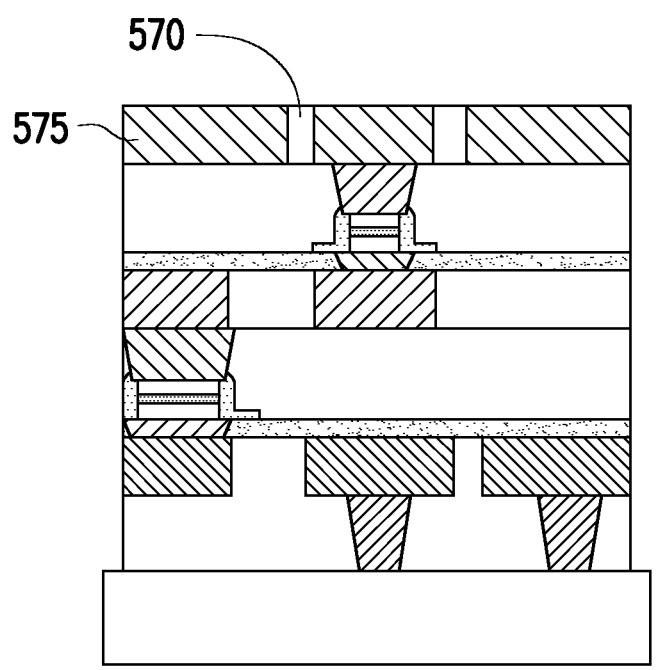

Then, similar to FIG. 9E, a sixth ILD layer 570 is formed over the fifth ILD layer 560 and a third metal wiring 575 is formed, as shown in FIG. 9G.

Figure 9H:
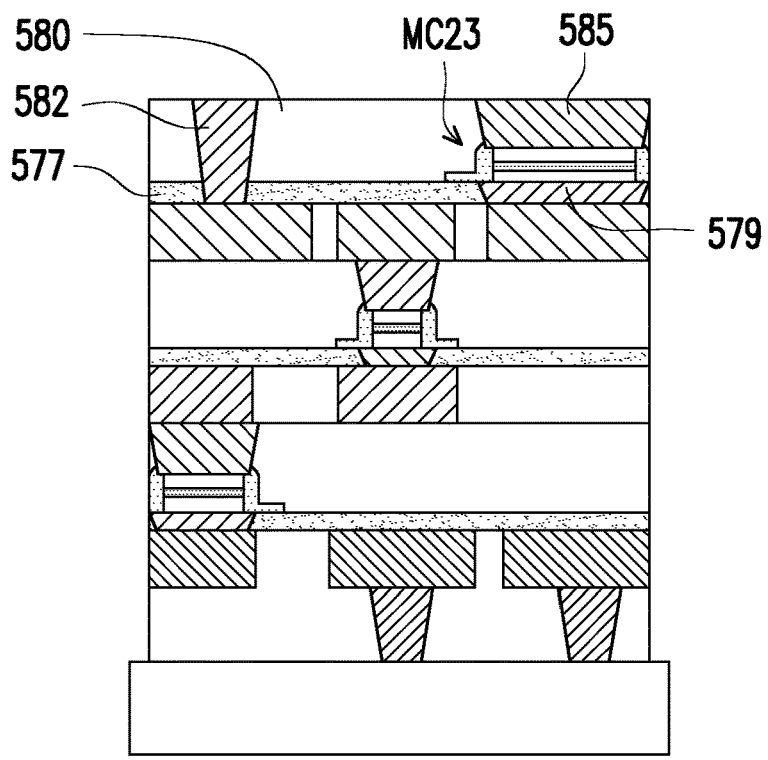

Further, by similar operations explained with FIGS. 9B-9C and 9F, an additional ILD layer or an etch stop layer 577 is formed over the sixth ILD layer 570, and a third lower electrode 579 is formed. Then, an MTJ film stack MC23 is formed. A seventh ILD layer 580 is formed to cover the MTJ film stack MC23 and a third upper electrode 585 is formed, as shown in FIG. 9H. In some embodiments, a contact plug 582 is formed.

Figure 9I:
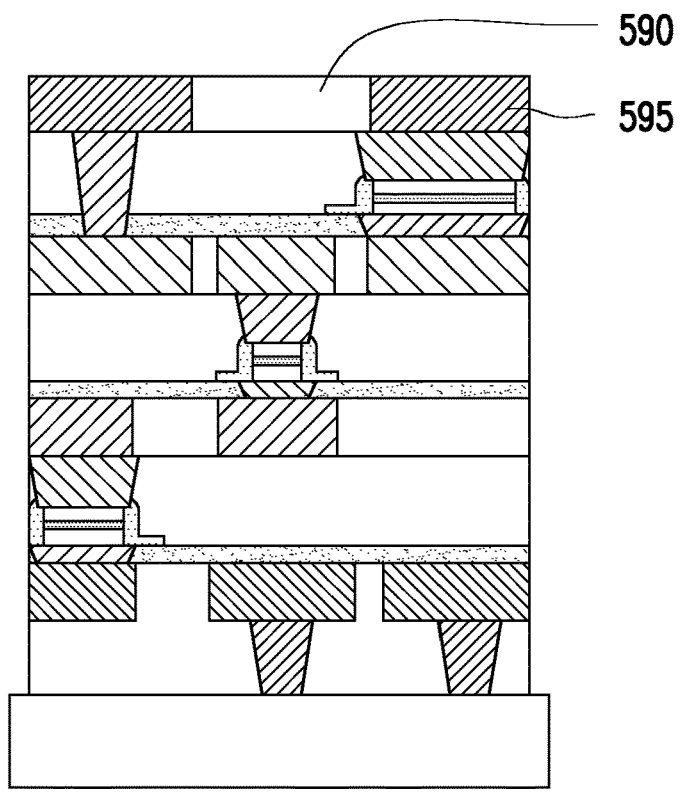

Then, similar to FIGS. 9E and 9G, an eighth ILD layer 590 is formed over the seventh ILD layer 580 and a fourth metal wiring 595 is formed, as shown in FIG. 9I.

In FIGS. 9A-9I, the sizes (at least one of the width and the thickness) of the MTJ film stacks MC21, MC22 and MC23 are different from each other. In some embodiments, the size of the MTJ film stack MC21 is larger than the size of the MTJ film stack MC22, which is smaller than the size of the MTJ film stack MC23. In other embodiments, the size of the MTJ film stack MC21 is smaller than the size of the MTJ film stack MC22, which is smaller than the size of the MTJ film stack MC23. In certain embodiments, the size of the MTJ film stack MC21 is larger than the size of the MTJ film stack MC22, which is larger than the size of the MTJ film stack MC23.

Figure 10:
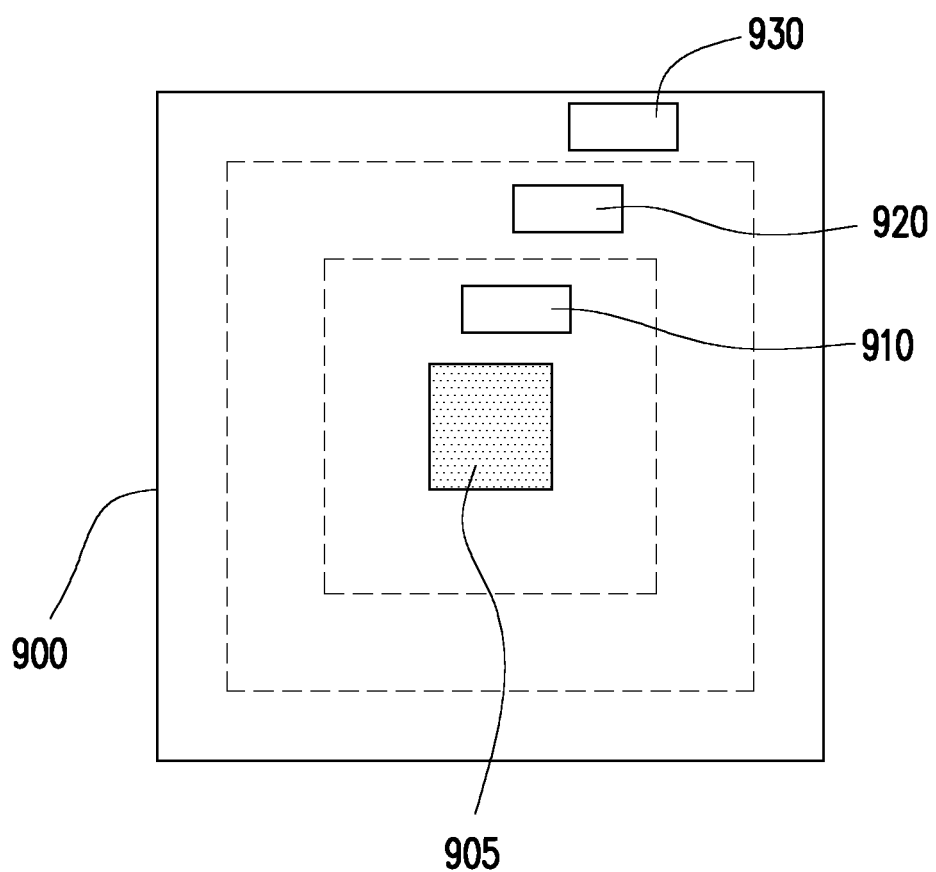
FIG. 10 shows a layout of a semiconductor device according to an embodiment of the present disclosure.

FIG. 10 shows a schematic layout of a semiconductor device including MRAMs according to an embodiment of the present disclosure.

In some embodiments, the semiconductor device 900 is a system-on-chip (SOC) including a core processor 905. The semiconductor device 900 also includes a first MRAM 910, a second MRAM 920 and a third MRAM 930. The first MRAM 910 includes an MTJ cell having a first size, the second MRAM 920 includes an MTJ cell having a second size and the third MRAM 930 includes an MTJ cell having a third size. It is noted that the number of MRAMs is not limited to three. In some embodiments, each of the three MRAMs has its own driver circuits and related peripheral circuits.

In some embodiments, the first size is smaller than the second size and the second size of smaller than the third size. As set forth above, when the size or the volume of the MTJ becomes smaller, the read/write speed becomes faster. In some embodiments, as shown in FIG. 10, the first MRAM 910 is located closer to the core processor 905 than the second MRAM 920 and the second MRAM 920 is located closer to the core processor 905 than the third MRAM 930.

In certain embodiments, the first MRAM 910 is used as a cache memory of the core processor 905.

It will be understood that not all advantages have been necessarily discussed herein, no particular advantage is required for all embodiments or examples, and other embodiments or examples may offer different advantages.

For example, in the present disclosure, the semiconductor device includes different MRAMs with MTJ cells having different sizes (width and/or thickness). By changing the size of the MTJ cells, it is possible to adjust the electrical properties of the MRAMs. Accordingly, the semiconductor device can have various functions with various MRAMs.

In accordance with an aspect of the present disclosure, a semiconductor device includes a magnetic random access memory (MRAM). The MRAM comprises a plurality of MRAM cells including a first type MRAM cell and a second type MRAM cell. Each of the plurality of MRAM cells includes a magnetic tunneling junction (MTJ) layer including a pinned magnetic layer, a tunneling barrier layer and a free magnetic layer. A size of the MTJ film stack of the first type MRAM cell is different from a size of the MTJ film stack of the second type MRAM cell. In one or more of the foregoing and following embodiments, a width of the MTJ film stack of the first type MRAM cell is different from a width of the MTJ film stack of the second type MRAM cell. In one or more of the foregoing and following embodiments, a thickness of the MTJ film stack of the first type MRAM cell is equal to a thickness of the MTJ film stack of the second type MRAM cell. In one or more of the foregoing and following embodiments, the width of the MTJ film stack of the second type MRAM cell is 1.1 to 50 times the width of the MTJ film stack of the first type MRAM cell. In one or more of the foregoing and following embodiments, a thickness of the MTJ film stack of the first type MRAM cell is different from a thickness of the MTJ film stack of the second type MRAM cell. In one or more of the foregoing and following embodiments, a width of the MTJ film stack of the first type MRAM cell is equal to a width of the MTJ film stack of the second type MRAM cell. In one or more of the foregoing and following embodiments, the thickness of the MTJ film stack of the second type MRAM cell is 1.1 to 20 times the thickness of the MTJ film stack of the first type MRAM cell. In one or more of the foregoing and following embodiments, the first type MRAM cell and the second type MRAM cell are disposed at a same device layer between a first wiring layer and a second wiring layer next to the first wiring layer in a vertical direction. In one or more of the foregoing and following embodiments, the plurality of MRAM cells further includes a third type MRAM cell, and a size of the MTJ film stack of the third MRAM cell is different from the size of the MTJ film stack of the first type MRAM cell and the size of the MTJ film stack of the second type MRAM cell. In one or more of the foregoing and following embodiments, a width of the MTJ film stack of the second type MRAM cell is 1.1 to 20 times a width of the MTJ film stack of the first type MRAM cell, and a width of the MTJ film stack of the third type MRAM cell is 1.1 to 20 times a width of the MTJ film stack of the second type MRAM cell. In one or more of the foregoing and following embodiments, a thickness of the MTJ film stack of the first type MRAM cell, a thickness of the MTJ film stack of the second type MRAM cell and a thickness of the MTJ film stack of the third type MRAM cell are equal to each other. In one or more of the foregoing and following embodiments, a thickness of the MTJ film stack of the second type MRAM cell is 1.1 to 20 times a thickness of the MTJ film stack of the first type MRAM cell, and a thickness of the MTJ film stack of the third type MRAM cell is 1.1 to 20 times a thickness of the MTJ film stack of the second type MRAM cell. In one or more of the foregoing and following embodiments, a width of the MTJ film stack of the first type MRAM cell, a width of the MTJ film stack of the second type MRAM cell and a width of the MTJ film stack of the third type MRAM cell are equal to each other. In one or more of the foregoing and following embodiments, sidewall spacers are disposed on opposing sides of at least one of the MTJ film stack of the first type MRAM cell and the second type MRAM cell, and an upper electrode is disposed on the at least one of the MTJ film stack and the sidewall spacers. In one or more of the foregoing and following embodiments, sidewall spacers are disposed on opposing sides of at least one of the MTJ film stack of the first type MRAM cell and the second type MRAM cell, and an upper electrode is disposed on the at least one of the MTJ film stack and partially penetrates in the sidewall spacers. In one or more of the foregoing and following embodiments, sidewall spacers are disposed on opposing sides of at least one of the MTJ film stack of the first type MRAM cell and the second type MRAM cell, and an upper electrode is disposed on the at least one of the MTJ film stack and not in contact with the sidewall spacers.

In accordance with another aspect of the present disclosure, a semiconductor device includes a magnetic random access memory (MRAM). The MRAM comprises a plurality of MRAM cells including a first type MRAM cell and a second type MRAM cell, and the first type MRAM cell is disposed at a first device layer and the second type MRAM cell is disposed at a second device layer different in a vertical direction from the first device layer. In one or more of the foregoing and following embodiments, each of the plurality of MRAM cells includes a magnetic tunneling junction (MTJ) layer including a pinned magnetic layer, a tunneling barrier layer and a free magnetic layer, and a size of the MTJ film stack of the first type MRAM cell is different from a size of the MTJ film stack of the second type MRAM cell. In one or more of the foregoing and following embodiments, the size of the MTJ film stack of the first type MRAM cell is smaller than the size of the MTJ film stack of the second type MRAM cell, and the first device layer is located above the second device layer. In one or more of the foregoing and following embodiments, the plurality of MRAM cells further includes a third type MRAM cell disposed at third first device layer, and the size of the MTJ film stack of the first type MRAM cell is smaller than the size of the MTJ film stack of the second type MRAM cell, the size of the MTJ film stack of the second type MRAM cell is smaller than a size of the MTJ film stack of the third type MRAM cell, and the first device layer is located above the second device layer, and the second device layer is located above the third device layer. In one or more of the foregoing and following embodiments, the first device layer is disposed between a first wiring layer and a second wiring layer above and next to the first wiring layer in a vertical direction, and the second device layer is disposed between a third wiring layer and a fourth wiring layer above and next to the third wiring layer in a vertical direction. In one or more of the foregoing and following embodiments, the second wiring layer is the same as the third wiring layer.

In accordance with another aspect of the present disclosure, a semiconductor device includes a core processor and a first magnetic random access memory (MRAM) and a second MRAM. The first MRAM includes a plurality of first type MRAM cells and the second MRAM includes a plurality of second type MRAM cells. Each of the plurality of first MRAM cells and the plurality of second MRAM cells includes a magnetic tunneling junction (MTJ) layer including a pinned magnetic layer, a tunneling barrier layer and a free magnetic layer. A size of the MTJ film stack of the plurality of first MRAM cell is smaller than a size of the MTJ film stack of the plurality of second MRAM cells. The first MRAM is located closer to the core processor than the second MRAM.

The foregoing outlines features of several embodiments or examples so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments or examples introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device including a magnetic random access memory (MRAM), wherein:
    a first interlayer dielectric (ILD) layer is disposed on a substrate;
    the MRAM comprises a plurality of MRAM cells including a first type MRAM cell, a second type MRAM cell and a third type MRAM cell,
    each of the plurality of MRAM cells includes a magnetic tunneling junction (MTJ) film stack including a pinned magnetic layer, a tunneling barrier layer and a free magnetic layer, a bottom electrode on which the MTJ film stack is disposed, and sidewall spacers disposed on opposing side faces of the MTJ film stack,
    a size of the MTJ film stack of the first type MRAM cell is different from a size of the MTJ film stack of the second type MRAM cell,
    the sidewall spacers are disposed on a part of an upper surface of the bottom electrode in each of the plurality of MRAM cells,
    an upper electrode is disposed on the MTJ film stack and the sidewall spacers,
    a second interlayer dielectric (ILD) layer is disposed on the sidewall spacers, and
    an etch stop layer disposed on the second ILD layer and a third interlayer dielectric (ILD) layer disposed on the etch stop layer are disposed on a side face of the upper electrode.

2. The semiconductor device of claim 1, wherein the upper electrode is in direct contact with the second ILD layer and the sidewall spacers.

3. The semiconductor device of claim 1, wherein the upper electrode partially penetrates the sidewall spacers of the MTJ film stack.

4. The semiconductor device of claim 1, wherein the bottom electrode includes a tapered shape such that a top side of the bottom electrode is larger than a bottom side of the bottom electrode.

5. The semiconductor device of claim 1, wherein the MTJ film stack includes a reversely tapered shape such that a top side of the bottom electrode is smaller than a bottom side of the bottom electrode.

6. The semiconductor device of claim 1, wherein the upper electrode includes a tapered shape such that a top side of the bottom electrode is larger than a top side of the bottom electrode.

7. The semiconductor device of claim 1, wherein a width of the upper electrode of the second type MRAM cell is 1.1 to 20 times a width of the upper electrode of the first type MRAM cell, and
a width of the upper electrode of the third type MRAM cell is 1.1 to 20 times a width of the upper electrode of the second type MRAM cell.

8. A semiconductor device including a magnetic random access memory (MRAM), wherein:
the MRAM comprises a plurality of MRAM cells including a first type MRAM cell, a second type MRAM cell and a third type MRAM cell,
the first type MRAM cell is disposed at a first device layer and the second type MRAM cell is disposed at a second device layer different in a vertical direction from the first device layer,
each of the plurality of MRAM cells includes a magnetic tunneling junction (MTJ) film stack disposed on a bottom electrode, and sidewall spacers disposed on opposing side faces of the MTJ film stack, and
the sidewall spacers are disposed on a part of an upper surface of the bottom electrode.

9. The semiconductor device of claim 8, wherein:
a width of the MTJ film stack of the second type MRAM cell is 1.1 to 20 times a width of the MTJ film stack of the first type MRAM cell, and
a width of the MTJ film stack of the third type MRAM cell is 1.1 to 20 times a width of the MTJ film stack of the second type MRAM cell.

10. The semiconductor device of claim 8, wherein:
an upper electrode of the second MRAM cells is disposed at the same height level of a lower electrode wiring of the first MRAM cells.

11. The semiconductor device of claim 8, wherein:
a lower electrode wiring of the second MRAM cells is disposed at the same height level of an upper electrode of the third MRAM cells.

12. The semiconductor device of claim 8, wherein:
a MTJ film stack of the second MRAM cells includes a tapered shape such that a width of a top side of the bottom electrode is different from a width of a bottom side of the bottom electrode, and
a MTJ film stack of the third MRAM cells includes a non-tapered shape such that a width of a top side of the bottom electrode is equal to a width of a bottom side of the bottom electrode.

13. The semiconductor device of claim 8, wherein:
a MTJ film stack of the second MRAM cells includes a first tapered shape and a MTJ film stack of the third MRAM cells includes a second tapered shape, such that the first tapered shape is different from the second tapered shape.

14. The semiconductor device of claim 8, wherein:
a MTJ film stack of the second MRAM cells includes a first tapered shape and a MTJ film stack of the third MRAM cells includes a second tapered shape, such that the first tapered shape is same as the second tapered shape.

15. A semiconductor device, comprising:
a core processor; and
a first magnetic random access memory (MRAM) and a second MRAM, wherein:
the first MRAM comprises a plurality of first type MRAM cells and the second MRAM comprises a plurality of second type MRAM cells,
each of the plurality of first MRAM cells and the plurality of second MRAM cells includes a magnetic tunneling junction (MTJ) film stack including a pinned magnetic layer, a tunneling barrier layer and a free magnetic layer, a bottom electrode on which the MTJ film stack is disposed, the bottom electrode embedded in an etch stop layer such that the etch stop layer is disposed on a side face of the bottom electrode and a sidewall spacer is disposed on a side face of the MTJ film stack and the etch stop layer,
a size of the MTJ film stack of the plurality of first MRAM cell is equal to a size of the MTJ film stack of the plurality of second MRAM cells,
the first MRAM is located closer to the core processor than the second MRAM, and
an upper electrode of the second MRAM cells is disposed at the same height level of a lower electrode wiring of the first MRAM cells.

16. The semiconductor device of claim 15, each of the plurality of first MRAM cells and the plurality of second MRAM cells further includes a first interlayer dielectric (ILD) layer is disposed on a substrate.

17. The semiconductor device of claim 16, each of the plurality of first MRAM cells and the plurality of second MRAM cells further includes:
an upper electrode is disposed on the MTJ film stack and the sidewall spacers, and
a second interlayer dielectric (ILD) layer is disposed on the sidewall spacers.

18. The semiconductor device of claim 17, wherein the upper electrode is in direct contact with the second ILD layer and the sidewall spacers.

19. The semiconductor device of claim 17, wherein the upper electrode partially penetrates the sidewall spacers of the MTJ film stack.

20. The semiconductor device of claim 17, wherein the bottom electrode includes a tapered shape such that a top side of the bottom electrode is larger than a bottom side of the bottom electrode.

* * * * *